US010912825B2

(12) United States Patent
Ni et al.

(10) Patent No.: US 10,912,825 B2
(45) Date of Patent: Feb. 9, 2021

(54) INFLUENZA VACCINES

(71) Applicant: KJ Biosciences LLC, College Station, TX (US)

(72) Inventors: Yawei Ni, College Station, TX (US); Jianhua Guo, College Station, TX (US)

(73) Assignee: KJ Biosciences LLC, College Station, TX (US)

( * ) Notice: Subject to any disclaimer, the term of this patent is extended or adjusted under 35 U.S.C. 154(b) by 0 days.

(21) Appl. No.: 16/246,876

(22) Filed: Jan. 14, 2019

(65) Prior Publication Data

US 2019/0142930 A1 May 16, 2019

Related U.S. Application Data

(62) Division of application No. 14/401,054, filed as application No. PCT/US2013/040829 on May 14, 2013, now abandoned.

(60) Provisional application No. 61/647,998, filed on May 16, 2012.

(51) Int. Cl.
| | | |
|---|---|---|
| *A61K 39/145* | (2006.01) | |
| *A61K 39/12* | (2006.01) | |
| *C12N 7/00* | (2006.01) | |
| *A61K 39/00* | (2006.01) | |

(52) U.S. Cl.
CPC ............ *A61K 39/145* (2013.01); *A61K 39/12* (2013.01); *C12N 7/00* (2013.01); *A61K 2039/525* (2013.01); *A61K 2039/5252* (2013.01); *A61K 2039/58* (2013.01); *A61K 2039/70* (2013.01); *C12N 2760/16134* (2013.01); *C12N 2760/16151* (2013.01); *C12N 2760/16161* (2013.01); *C12N 2760/16234* (2013.01)

(58) Field of Classification Search
None
See application file for complete search history.

(56) References Cited

U.S. PATENT DOCUMENTS

| | | | |
|---|---|---|---|
| 7,608,268 B2 | 10/2009 | Carter et al. | |
| 2004/0006001 A1 | 1/2004 | Carter et al. | |
| 2007/0258889 A1 | 11/2007 | Douglas et al. | |
| 2010/0172934 A1* | 7/2010 | Krenn .................. | A61K 39/145 424/204.1 |
| 2011/0261536 A1 | 10/2011 | Feichtinger et al. | |
| 2011/0273202 A1 | 11/2011 | Kim et al. | |
| 2013/0171181 A1 | 7/2013 | Ni | |

FOREIGN PATENT DOCUMENTS

| | | |
|---|---|---|
| JP | 5-299148 | 11/1993 |
| WO | 2006/028238 | 3/2006 |
| WO | 2011/082087 | 7/2011 |
| WO | 2013/183478 | 12/2013 |

OTHER PUBLICATIONS

Scholtissek, Stability of infectious influenza A viruses to treatment at low pH and Heating, 1985, Archives of Virology, vol. 85, pp. 1-11.*
Jonges et al., Influenza virus inactivation for studies of antigenicity and phentotypic neuraminidase inhibitor resistance profiling, 2010, Journal of Clinical Microbiology, vol. 48, No. 3.*
Wanaratana et al., The inactivation of aivan influenza virus subtype H1N1 isolated from chickens in Thailand by chemical and physical treatments, 2010, Veterinary Microbiology, vol. 140, pp. 43-48.*
Almiron, M., et al., "A novel DNA-binding protein with regulatory and protective roles in starved *Escherichia coli*," Genes Dev., vol. 6, 1992, pp. 2646-2654.
Beignon, A.-S., et al., "A peptide vaccine administered transcutaneously together with cholera toxin elicits potent neutralising anti-FMDV antibody responses," Veterinary immunology and immunopathology, vol. 104, 2005, pp. 273-280.
Brandt, L., et al., "Key Epitopes on the ESAT-6 Antigen Recognized in Mice During the Recall of Protective Immunity to *Mycobacterium tuberculosis*," The Journal of Immunology, vol. 157, 1996, pp. 3527-3533.
Bullough, P.A., et al., "Structure of influenza haemagglutinin at the pH of membrane fusion," Nature, vol. 371, 1994, pp. 37-43.
Burton, D.R., et al., "A Boost for HIV Vaccine Design," Science, vol. 329, 2010, pp. 770-773.
Caldeira, J., et al., "Immunogenic display of diverse peptides, including a broadly cross-type neutralizing human papillomavirus L2 epitope, on virus-like particles of the RNA bacteriophage PP7," Vaccine, vol. 28, 2010, pp. 4384-4393.
Carr, C.M., et al., Influenza hemagglutinin is spring-loaded by a metastable native conformation, PNAS, vol. 94, No. 26, 1997, pp. 14306-14313.
Chackerian, B., "Virus-like particles: flexible platforms for vaccine development," Expert Rev. Vaccines, vol. 6, No. 3, 2007, pp. 381-390.
Cheever, M.A., et al., "The Prioritization of Cancer Antigens: A National Cancer Institute Pilot Project for the Acceleration of Translational Research," Clinical Cancer Research, vol. 15, 2009, pp. 5323-5337.
Chun, S., et al., "Universal antibodies and their applications to the quantitative determination of virtually all subtypes of the influenza A viral hemagglutinins," Vaccine, vol. 26, 2008, pp. 6068-6076.

(Continued)

*Primary Examiner* — Benjamin P Blumel
(74) *Attorney, Agent, or Firm* — Meunier Carlin & Curfman LLC

(57) ABSTRACT

An influenza vaccine comprising an influenza hemagglutinin-containing antigen which is subjected to a treatment at a suitable low pH or other suitable conditions to obtain a suitable degree of loss of potency, and the method of making it are provided. The vaccine not only induces an increased cross-reactive immune response and cross protection, but can also induce a strain-specific immune response and protection like current inactivated vaccines. A method of administering influenza vaccines is also provided to induce an increased cross-reactive immune response and cross protection, which is especially suitable for use in emergency situations such as a pandemic.

24 Claims, 8 Drawing Sheets

(56) References Cited

OTHER PUBLICATIONS

Corti, D., et al., "A Neutralizing Antibody Selected from Plasma Cells That Binds to Group 1 and Group 2 Influenza A Hemagglutinins," Science, vol. 333, No. 6044, 2011, pp. 850-866.

Cox, R.J., et al., "Evaluation of a virosomal H5N1 vaccine formulated with Matrix M™ adjuvant in a phase I clinical trial," Vaccine, vol. 29, Issue 45, 2011, pp. 8049-8059.

De Bernard, M., et al., "The immune modulating activity of the *Helicobacter pylori* HP-NAP: Friend or foe?," Toxicon, vol. 56, 2010, pp. 1186-1192.

Denis, J., et al., "Development of a universal influenza A vaccine based on the M2e peptide fused to the papaya mosaic virus (PapMV) vaccine platform," Vaccine, vol. 26, 2008, pp. 3395-3403.

Du, L., et al., "Research and development of universal influenza vaccines," Microbes and Infection, vol. 12, No. 4, 2010, pp. 280-286.

Ekiert, D.C., et al., "Antibody recognition of a highly conserved influenza virus epitope," Science, vol. 324, 2009, pp. 246-251.

El Bakkouri, K., et al., Universal Vaccine Based on Ectodomain of Matrix Protein 2 of Influenza A: Fc Receptors and Alveolar Macrophages Mediate Protection, The Journal of Immunology, vol. 186, No. 2, 2011, pp. 1022-1031.

Fiers, W., et al., "M2e-based universal influenza A vaccine," Vaccine, vol. 27, Issue 45, 2009, pp. 6280-6283.

Fiore, A.E., et al., "Seasonal Influenza Vaccines," Current Topics in Microbiology and Immunology, vol. 333, 2009, pp. 43-82.

Foo, D.G., et al., "Identification of neutralizing linear epitopes from the VP1 capsid protein of Enterovirus 71 using synthetic peptides," Virus Res., vol. 125, No. 1, 2007, pp. 61-68.

Fouchier, R., et al., "Characterization of a Novel Influenza A Virus Hemagglutinin Subtype (H16) Obtained from Black-Headed Gulls," Journal of Virology, vol. 79, No. 5, 2005, pp. 2814-2822.

Fukuda, K., et al., "Inactivated Influenza Vaccines," Vaccines: Chapter 17, Plotkin et al., eds., 4$^{th}$ edition, 2004, pp. 339-370.

Galili, U., et al., "A Unique Natural Human IgG Antibody with Anti-α-Galactosyl Specificity," J. Exp. Med., vol. 160, 1984, pp. 1519-1531.

Garçon, N., et al., "Development and evaluation of AS03, an Adjuvant System containing α-tocopherol and squalene in an oil-in-water emulsion," Expert Review of Vaccines, vol. 11, No. 3, 2012, pp. 349-366.

Gauss, G.H., et al., "Structure of the DPS-Like Protein from *Sulfolobus solfataricus* Reveals a Bacterioferritin-Like Dimetal Binding Site within a DPSLike Dodecameric Assembly," Biochemistry, vol. 45, No1. 36, 2006, pp. 10815-10827.

Genbank ID AE006642.1, 2004.
Genbank ID AF536179.1, 2003.
Genbank ID CY033622.1, 2008.
Genbank ID CY033623.1, 2008.
Genbank ID X69337.1, 2003.

Gerhard, W., et al., "Prospects for Universal Influenza Virus Vaccine," Emerging Infectious Diseases, vol. 12, No. 4, 2006, pp. 569-574.

Gilbert, S.C., "Advances in the development of universal influenza vaccines," Influenza Journal, 2012, pp. 750-758.

Grant, R.A., et al., "The crystal structure of Dps, a ferritin homolog that binds and protects DNA," Nature Structural Biology, vol. 5, No. 4, 1998, pp. 294-303.

Grgacic, E., et al., "Virus-like particles: Passport to immune recognition," Methods, vol. 40, 2006, pp. 60-65.

Haikarainen, T., et al., "Dps-like proteins: structural and functional insights into a versatile protein family," Cellular and Molecular Life Sciences, vol. 67, 2010, pp. 341-351.

Heddle, J.G., "Protein cages, rings and tubes: useful components of future nanodevices?," Nanotechnology, Science and Applications, vol. 1, 2008, pp. 67-78.

Heiny, A.T., et al., "Evolutionarily Conserved Protein Sequences of Influenza A Viruses, Avian and Human, as Vaccine Targets," PLoS One, vol. 2, Issue 11, 2007, 14 pages.

Huleatt, J.W., et al., "Potent immunogenicity and efficacy of a universal influenza vaccine candidate comprising a recombinant fusion protein linking influenza M2e to the TLR5 ligand flagellin," Vaccine, vol. 26, 2007, pp. 201-214.

Ilari, A., et al., "The dodecameric ferritin from *Listeria innocua* contains a novel intersubunit iron-binding site," Nature Structural Biology, vol. 7, No. 1, 2000, pp. 38-43.

Ionescu, R.M., et al., Pharmaceutical and Immunological Evaluation of Human Papillomavirus Viruslike Particle as an Antigen Carrier, Journal of Pharmaceutical Sciences, vol. 95, No. 1, 2006, pp. 70-79.

Jakubovics, N.S., et al., "Differential binding specificities of oral streptococcal antigen I/II family adhesions for human or bacterial ligands," Molecular Biology, vol. 55, No. 5, 2005, pp. 1591-1605.

Kanodia, S., et al., "Peptide-based vaccines for cancer: realizing their potential," Expert Review of Vaccines, vol. 7, 2008, pp. 1533-1545.

Karanam, B., et al., "Developing vaccines against minor capsid antigen L2 to prevent papillomavirus infection," Immunol. Cell Biol., vol. 87, 2009, 28 pages.

Kashyap, A.K., et al., "Combinatorial antibody libraries from survivors of the Turkish H5N1 avian influenza outbreak reveal virus neutralization strategies," PNAS, vol. 105, No. 16, 2008, pp. 5986-5991.

Kim, K-K, et al., "Crystal structure of a small heat-shock protein," Nature, vol. 394, 1998, pp. 595-599.

Kim, S-G, et al., "Crystal Structure of Dps-1, a Functionally Distinct Dps Protein from *Deinococcus radiodurans*," Journal of Molecular Biology, 2006, vol. 361, 2006, pp. 105-114.

Lambert, L.C., et al., "Influenza Vaccines for the Future," The New England Journal of Medicine, vol. 363, 2010, pp. 2036-2044.

Liepold, L., et al., Viral Capsids as MRI Contrast Agents, Magnetic Resonance in Medicine, vol. 58, 2007, pp. 871-879.

Luo, M., "Influenza Virus Entry," Advances in Experimental Medicine and Biology: Chapter 9, 2011, pp. 201-221.

Nabel, G.J., et al., "Induction of unnatural immunity: prospects for a broadly protective universal influenza vaccine," Nature Medicine, vol. 16, No. 12, 2010, pp. 1389-1391.

Neirynck, S., et al., "A universal influenza A vaccine based on the extracellular domain of the M2 protein," Nature Medicine, vol. 5, No. 10, 1999, pp. 1157-1163.

Oka, Y., et al., "WT1 peptide vaccine for the treatment of cancer," Current Opinion in Immunology, vol. 20, 2008, pp. 211-220.

Oscherwitz, J., et al., "A Synthetic Peptide Vaccine Directed against the 2β2-2β3 Loop of Domain 2 of Protective Antigen Protects Rabbits from Inhalation Anthrax," The Journal of Immunology, vol. 185, 2010, pp. 3661-3668.

Osterholm, M.T., et al., "Efficacy and effectiveness of influenza vaccines: a systematic review and meta-analysis," Lancet Infectious Diseases, vol. 12, Issue 1, 2012, pp. 36-44.

Paek, S-H, et al., "Development of Rapid One-Step Immunochromatographic Assay," Methods, vol. 22, 2000, pp. 53-60.

Piao, H., et al., "Induction of paranodal myelin detachment and sodium channel loss in vivo by *Campylobacter jejuni* DNA-binding protein from starved cells (C-Dps) in myelinated nerve fibers," Journal of the Neurological Sciences, vol. 288, 2010, pp. 54-62.

Pozsgay, V., et al., "Conjugation Methods toward Synthetic Vaccines," Carbohydrate-Based Vaccines: Chapter 3, ACS Division of Carbohydrate Chemistry, ACS Symposium Series 989, René Roy (ed.), 2008, pp. 36-70.

Pumpens, P., et al., "Hepatitis B core particles as a universal display model: a structure-function basis for development," FEBS Letters, vol. 442, 1999, pp. 1-6.

Quan, F-S, et al., "Immunogenicity of low-pH treated whole viral influenza vaccine," Virology, vol. 417, 2011, pp. 196-202.

Rappuoli, R., "The challenge of developing universal vaccines," F1000 Medicine Reports, vol. 3, No. 16, 2011, 6 pages.

Roy, S., et al., "Role of N and C-terminal Tails in DNA Binding and Assembly in Dps: Structural Studies of *Mycobacterium smegmatis* Dps Deletion Mutants," Journal of Molecular Biology, vol. 370, 2007, pp. 752-767.

(56) References Cited

OTHER PUBLICATIONS

Russell, R.S., et al., "Advantages of a single-cycle production assay to study cell culture-adaptive mutations of hepatitis C virus," PNAS, vol. 105, No. 11, 2008, pp. 4370-4375.
Santosuosso, M., et al. "Intranasal Boosting with an Adenovirus-Vectored Vaccine Markedly Enhances Protection by Parenteral *Mycobacterium bovis* BCG Immunization against Pulmonary Tuberculosis," Infection and Immunity, vol. 74, No. 8, 2006, pp. 4634-4643.
Shi, W., et al., "Structural Characterization of HIV gp41 with the Membrane-proximal External Region," The Journal of Biological Chemistry, vol. 285, No. 31, 2010, pp. 24290-24298.
Skehel, J.J., et al., "Receptor Binding and Membrane Fusion in Virus Entry: The Influenza Hemagglutinin," Annual Review of Biochemistry, vol. 69, 2000, pp. 531-569.
Speir, J.A., et al., "Structures of the native and swollen forms of cowpea chlorotic mottle virus determined by X-ray crystallography and cryo-electron microscopy," Structure, vol. 3, No. 1, 1995, pp. 63-78.
Staneková, et al., "Conserved epitopes of influenza A virus inducing protective immunity and their prospects for universal vaccine development," Virology Journal, vol. 7, No. 351, 2010, 13 pages.
Stillman, T.J., et al., "The crystal structures of *Lactococcus lactis* MG1363 Dps proteins reveal the presence of an N-terminal helix that is required for DNA binding," Molecular Microbiology, vol. 57, No. 4, 2005, pp. 1101-1112.
Sui, J., et al., "Structural and functional bases for broad-spectrum neutralization of avian and human influenza A viruses," Nat Struct Mol Biol., vol. 16, No. 3, 2009, pp. 265-273.
Swalley, S.E., et al., "Full-Length Influenza Hemagglutinin $HA_2$ Refolds into the Trimeric Low-pH-Induced Conformation," Biochemistry, vol. 43, 2004, pp. 5902-5911.
Swiss-Prot Accession No. P0ABT2, 1992.
Swiss-Prot Accession No. P0C558, 2003.
Swiss Prot Accession No. P03519, 1992.
Swiss-Prot Accession No. P95855, 2001.
Swiss Prot Accession No. B1S132, 2007.
Swiss Prot Accession No. P43313, 1995.
Swiss Prot Accession No. P80725, 1997.
Swiss Prot Accession No. Q7CQV9, 2001.
Swiss Prot Accession No. Q9RS64, 2005.
Swiss Prot Accession No. Q32191, 1994.
Swiss Prot Accession No. Q84102, 1990.
Teneberg, S., et al., "Carbohydrate Binding Specificity of the Neutrophil-activating Protein of *Helicobacter pylori*," The Journal of Biological Chemistry, vol. 272, No. 30, 1997, pp. 19067-19071.
Verdoliva, A., et al., "Simplified β-amyloid peptides for safer Alzheimer vaccines development," Human Vaccines, vol. 6, No. 11, 2010, pp. 936-947.
Wang, K., et al., "Expression and purification of an influenza hemagglutinin—one step closer to a recombinant protein-based influenza vaccine," vol. 24, 2006, pp. 2176-2185.
Whittle, J., et al., "Broadly neutralizing human antibody that recognizes the receptor-binding pocket of influenza virus hemagglutinin," PNAS, vol. 108, No. 34, 2011, pp. 14216-14221.
Wiedenheft, B., et al., "An archaeal antioxidant: Characterization of a Dps-like protein from *Sulfolobus solfataricus*," PNAS, vol. 102, No. 30, 2005, pp. 10551-10556.
Wiedenheft, B., et al., "Bioprospecting in high temperature environments; application of thermostable protein cages," Soft Matter, vol. 3, 2007, pp. 1091-1098.
Wood, J.M., et al., "An improved single-radial-immunodiffusion technique for the assay of influenza haemagglutinin antigen: application for potency determinations of inactivated whole virus and subunit vaccines," Journal of Biological Standard, vol. 5, No. 3, 1977, pp. 237-247.
Wood, J.M., et al., "Single-radial-immunodiffusion potency tests of inactivated influenza vaccines for use in man and animals," Develop. biol Standard, vol. 64, 1986, pp. 169-177.
Zhao, G., et al., "Iron and Hydrogen Peroxide Detoxification Properties of DNA-binding Protein from Starved Cells. A Ferritin-Like DNA-Binding Protein of *Escherichia coli*," The Journal of Biological Chemistry, vol. 277, 2002, pp. 27689-27696.
U.S. Appl. No. 13/520,253, filed Dec. 22, 2010.
Notice of Allowance, dated Oct. 2, 2015, received in connection with U.S. Appl. No. 13/520,253.
Final Office Action, dated Jul. 8, 2014, received in connection with U.S. Appl. No. 13/520,253.
Non-final Final Office Action, dated Dec. 4, 2013, received in connection with U.S. Appl. No. 13/520,253.
Restriction Requirement, dated Jul. 19, 2013, received in connection with U.S. Appl. No. 13/520,253.
International Preliminary Report on Patentability, dated Apr. 20, 2014, received in connection with International Patent Application No. PCT/US2013/040829.
International Search Report, dated Nov. 7, 2013, received in connection with International Patent Application No. PCT/US2013/040829.
Written Opinion, dated Nov. 7, 2013, received in connection with International Patent Application No. PCT/US2013/040829.
International Preliminary Report on Patentability and Written Opinion, dated Jul. 4, 2012, received in connection with International Patent Application No. PCT/US2010/061906.
International Search Report, dated Jun. 1, 2011, received in connection with International Patent Application No. PCT/US2010/061906.
Wanaratana et al., The inactivation of avian influenza virus subtype H5N1 isolated from chickens in Thailand by chemical and physical treatments, 2010, Veterinary Microbiology, vol. 140, pp. 43-48.
Jonges et al., Influenza Virus Inactivation for Studies of Antigenicity and Phenotypic Neuraminidase Inhibitor Resistance Profiling, 2010, Journal of Clinical Microbiology, vol. 48, No. 3, pp. 928-940.

\* cited by examiner

Figure 6

INFLUENZA VACCINES

CROSS-REFERENCE TO RELATED APPLICATIONS

This application is a divisional of U.S. patent application Ser. No. 14/401,054 filed Nov. 13, 2014, which is a 371 of PCT/US2013/040829 filed May 14, 2013, which claims benefit of provisional application No. 61/647,998 filed May 16, 2012, all of which are incorporated herein in their entirety.

GOVERNMENT SUPPORT

This invention was made with government support under Grant No. AI092923 awarded by the National Institutes of Health. The U.S. Government has certain rights in the invention.

FIELD OF THE INVENTION

The present invention relates generally to the field of medicine, and specifically to microbiology, immunology, and vaccines, and more specifically, influenza vaccines.

BACKGROUND OF THE INVENTION

There are three types of influenza viruses, A, B, and C. Influenza A and B viruses are responsible for most of infections and related diseases in humans and animals. Influenza A virus has been associated with all influenza pandemics with the latest one in 2009. Influenza viruses have two major glycoproteins anchored on its membrane envelope, hemagglutinin (HA) and neuraminidase (NA). The HA is responsible for mediating virus entry into target cells through binding to cell receptors and mediating fusion between viral and cell membranes. The HA is also the major target of host immune responses and the protective antigen for current licensed vaccines.

Influenza viruses undergo constant genetic changes due to its error prone replication and ability to reassort genome segments, resulting in constant antigenic changes in HA and emergence of variant or new virus strains. The past pandemics have all been associated with emergence of variant or new virus strains, to which human populations have little or no pre-existing immunity. Based on antigenic characteristics of HA and NA, influenza A viruses are divided into 16 HA (H1-H16) and 9 NA (N1-N9) subtypes, whereas influenza B viruses are divided into two broad lineages. Viruses within the same subtype can still be antigenically divergent or heterologous as the result of constant antigenic changes. The 16 HA subtypes fall into two broad phylogenetic groups (I and II) based on sequence homology of HA proteins, each of which can be further divided into three (H1, H2, H5, and H6; H8, H9 and H12; H11, H13, and H16) and two clades (H3, H4, and H14; H7, H10, and H15) (Russell et al., Natl Acad Sci USA. 105:17736-17741, 2008).

Influenza Vaccines

Current licensed influenza vaccines are primarily the trivalent inactivated vaccines (TIV) containing antigens from two HA subtypes (H1 and H3) and one type B virus (Fukuda et al., In Vaccines. Plotkin et al (ed.), 4th ed. pp 339-370, 2003, Saunders. Philadelphia; Fiore et al., Curr Top Microbiol Immunol. 333:43-82, 2009). Recently, a quadrivalent inactivated vaccine (QIV) has been licensed, which is same as TIV, but incorporates an additional B virus. It has not been used widely. These vaccines are strain-specific. To match viruses in circulation, vaccine strains are updated every year. For protection against pandemics, monovalent inactivated vaccines targeting the pandemic virus are also produced such as the one for the 2009 H1N1 pandemic. The efficacy of current TIVs is only moderate with an average efficacy of 59% in adults aged 18-65 years (Osterholm et al., Lancet Infect Dis. 12:36-44, 2012), which could be even lower against the poorly matched variant viruses. Thus, great needs exist to improve the current TIVs.

The inactivated vaccines are manufactured using chicken eggs or cultured avian or mammalian cells including MDCK and Vero. The manufacturing process involves growing, harvesting, and purification of viruses. The viruses are inactivated during the manufacturing process, e.g., at the step of harvesting or after virus purification. The inactivation may be achieved using various chemical agents and physical means. The agents include formaldehyde, glutaraldehyde, beta-propiolactone, and Triton X-100, of which formaldehyde is most widely used. The physical means include heat, gamma-irradiation, and UV light. Purified inactivated viruses may be used directly as the whole virus (WV) antigen for vaccines or may be split to subvirion components to produce the split vaccines. The split subcomponents may be further purified to produce the subunit vaccine. Currently, TIVs made of the split or subunit antigens are most widely used. The inactivated WV vaccine is also being used, which may be preferred against pandemics since it is more immunogenic and can be produced faster as compared to split or subunit vaccines.

The HA is the protective antigen. The inactivated vaccines are standardized based on the amount of HA protein, which serves as the potency indicator for the vaccines. It is determined by the single radial diffusion (SRD) test using polyclonal antibodies specific to HA of the virus strain to be tested and used in the vaccine. The SRD is performed on an agar plate containing the anti-HA antibodies where the test antigen is placed into small round wells formed in the agar along with the reference antigen (Wood et al., J Biol Stand. 5:237-247, 1977; Dev Biol Stand. 64:169-177, 1986). The diffusion of antigen into agar allows the binding of antigen and antibody and consequently formation of a precipitation ring. The size of the ring reflects the amount of HA present in the antigen or vaccines. For current TIVs, the potency standard is 15 or 60 µg HA for each of three strains per vaccine dose for adults or elderly populations. The immunogenicity of the TIVs has been evaluated extensively. The potency standard is correlated with induction of a certain level of protective immune responses as measured by hemagglutination inhibition (HAI) and neutralization test (NT). A HAI titer of >1:40 is generally considered as the protective threshold in humans.

Besides the inactivated vaccines, other forms of influenza vaccines are being developed (Lambert and Fauci, N Engl J Med. 363:2036-2044, 2010). These include recombinant HA protein and virus-like particles (VLP) consisting of HA protein either alone or in combination with other viral proteins. Recently, a trivalent vaccine based on recombinant HA has been licensed. The recombinant HA protein and VLPs can be produced using various different expression systems, including bacteria, avian or mammalian cells, baculovirus, and plants. They are non-living or not made from infectious materials and therefore do not go through the inactivation step. However, the potency of these vaccines is also based on the amount of HA as determined by SRD, although the potency standard for these vaccines may vary based on the immunogenicity and effectiveness of the antigen.

Structure and Function of the HA Protein

The HA is a trimeric protein consisting of three identical subunits (Skehel and Wiley, Annu. Rev. Biochem. 69:531-569, 2000; Luo, Adv Exp Med Biol. 726:201-221, 2012). Each subunit consists of two parts, HA1 and HA2, as the result of protease cleavage of the precursor HA0. The HA1 and HA2 remain associated together through disulfide and hydrogen bonding. The three HA subunits together form the umbrella-shaped HA molecule with the globular head formed by HA1 and the stem region mostly by HA2. The HA1 bears the receptor binding site and is responsible for binding to host cells, whereas the HA2 consists of the fusion peptide and long helix domains and is responsible for mediating cell fusion (Bullough et al., Nature. 371:37-43, 1994). HA1 is the primary target of immune responses as compared to HA2 which is covered underneath the HA1 and less immunogenic. Following the binding to host cells, viruses are taken into endosome where they are exposed to the low pH (~5.0) environment. At this low pH, HA undergoes irreversible and drastic conformational changes, including dissociation of HA1 globular head and rising of the re-folded HA2 stem (Skehel and Wiley, Annu. Rev. Biochem. 69:531-569, 2000). These conformational changes lead to fusion of viral and cellular membranes, resulting in delivery of viral genome into cytoplasma.

Conserved Antigen Domains and Development of Influenza Vaccines with Broad-Spectrum Protection The constant antigenic changes of influenza viruses pose a great challenge to developing vaccines for controlling influenza epidemics and pandemics. Current TIVs (H1, H3, and B) are strain-specific and are not suited for controlling pandemics. Thus, an influenza vaccine which provides a broad-spectrum protection against divergent subtypes of influenza viruses is urgently needed to provide better control of influenza epidemics and an effective countermeasure against pandemics.

One key strategy for developing a broadly protective vaccine is to target the highly conserved antigen domains so that specific antibodies generated are cross-reactive, i.e., capable of reacting with heterologous viruses from the same or different subtypes to provide cross protection (Heiny et al., PLoS One. 2:e1190, 2007; Du et al., Microbes Infect. 12:280-286, 2010; Gilbert, Influenza and other respiratory viruses. 10.1111/irv.12013, 2012). Although the HA constantly undergoes antigenic changes, highly conserved domains can be found in both HA1 and HA2. However, the HA2 is much more conserved than the HA1 (Fouchier et al., J Virol. 79:2814-22, 2005; Gerhard et al., Emerg Infect Dis. 12:569-574, 2006). The average percent identify for HA2 is at least 92% within each individual subtype or 87% between two closely related subtypes from each of the four clades analyzed (Fouchier et al., J Virol. 79:2814-22, 2005). A monoclonal antibody that recognizes the receptor binding site of HA1 has been shown to be capable of neutralizing 30 of the 36 H1N1 virus strains tested (Whittle et al., Proc Natl Acad Sci USA. 108:14216-14221, 2011). On the other hand, several highly conserved domains in the stem region of HA2 have been identified using monoclonal antibodies (Kashyap et al., Proc Natl Acad Sci USA. 105:5986-91, 2008; Ekiert et al., Science. 324:246-51, 2009; Sui et al., Nat Struct Mol Biol. 16:265-73, 2009; Corti et al., Science. 333:850-856, 2011). The highly conserved domains found in HA2, M2 and other viral proteins have been major targets for development of broadly protective or universal influenza vaccines (Stanekova and Vareckova, Virol J. 7:351, 2010; Gilbert, Influenza and other respiratory viruses. 10.1111/irv.12013, 2012).

The cross-reactive antibodies against highly conserved domains can be produced by vaccination with current vaccines or after infection, but only at low levels not sufficient to provide protection. Thus, the key objective of broadly protective vaccines is to increase cross-reactive antibody responses against such domains. The cross-reactive antibodies can be neutralizing or non-neutralizing. The neutralizing antibodies can prevent infection by preventing viruses from entering cells. The non-neutralizing antibodies may not prevent infection, but can reduce the incidence and severity of the disease. Studies with the highly conserved M2e domain of the M2 protein have shown that non-neutralizing cross-reactive antibodies can be highly protective and reduce virus shedding (Stanekova and Vareckova, Virol J. 7:351, 2010; El Bakkouri et al., J Immunol. 186:1022-1031, 2011).

It is recognized that a full-spectrum or true universal influenza vaccine that can provide protection against all influenza viruses (A and B) and replace all current vaccines would be ideal. However, it is a formidable task and may take a long development process before it can be approved for use in people (Nabel and Fauci, Nat Med. 16:1389-91, 2010; Rappuoli, F1000 Med Rep. 3:16, 2011). Thus, a broad-spectrum vaccine which can at least provide protection against major subtypes that are important to seasonal epidemics and have a greater potential to cause future pandemics including H1, H3, and H5 may be developed first to meet the current and immediate need. In light of the fact that influenza epidemics are a constant annual event and the next pandemic may occur at any time, the need for accelerated development of broad-spectrum and universal vaccines for protection against possible future pandemics and better control of the epidemics is critical and urgent for the well-being of world populations.

SUMMARY OF THE INVENTION

Therefore, the present invention provides an influenza vaccine which can not only provide an increased cross-reactive immune response and cross-protection against variant or heterologous viruses, but also a strain-specific immune response and protection against viruses contained in the vaccine like current inactivated vaccines. This vaccine comprises an influenza HA-containing antigen which is subjected to a treatment at a suitable low pH or other suitable conditions to obtain a suitable degree of loss of potency. The present invention revealed that the potency of influenza HA-containing antigens could be gradually reduced by up to 100% by low pH treatment in direct correlation with treatment conditions, and only the antigens with a suitable degree of loss of potency obtained under appropriate low pH treatment conditions induced the increased cross-reactive antibody responses and cross protection which distinctively was associated with the increased cross reaction with HA2, the highly conserved part of HA. The loss of potency may be correlated with and indicated by a functionally equivalent alternative measurement for antigenic or structural changes. These antigens can be readily formulated to meet the potency standard as a vaccine by compensating the partial potency loss with an appropriate amount of additional antigens or an adjuvant. The resulting vaccine can therefore provide the same level of strain-specific immune responses and protection against viruses contained in the vaccine as with the untreated antigen or like current inactivated vaccines, and at the same time also an increased cross-reactive immune response and cross protection against viruses not contained in the vaccine, including the possible pandemic as well as seasonal variant viruses.

This new influenza vaccine can be made with single or multiple antigens. It is highly suited for production of a new TIV based on the same three antigens (H1, H3, and B). By incorporating treated antigens from all three or at least H1 and H3 strains, the new TIV can induce even broader cross-reactive immune responses, especially considering that H1 and H3 subtypes belong separately to the two different phylogenetic groups. The same can be achieved with the recently licensed quadrivalent inactivated vaccine (QIV) which is same as TIV, but incorporates an additional B virus antigen. When formulated to meet the potency standard, the new TIV or QIV will not only fulfill its original indication—the strain-specific protection against the viruses contained in the vaccine, but also provide a broad cross-reactive immune response and cross protection against viruses not contained in the vaccine, thereby providing better control of seasonal epidemics as well as protection against possible pandemics. Antigens from additional subtypes or clades of both phylogenetic groups can be incorporated to further broaden and strengthen the cross reaction and protection.

The present invention further provides a method for inducing an increased cross-reactive immune response and cross protection against influenza viruses in a human or animal by administering an effective dose of an influenza vaccine comprising an influenza HA-containing antigen which obtains a suitable degree of loss of potency by treatment at a suitable low pH or other suitable conditions. The present invention further presents a method for inducing both a strain-specific immune response and protection and an increased cross-reactive immune response and cross protection against influenza viruses in a human or animal by administering an effective dose of this vaccine which is further formulated to meet the potency standard.

The present invention further provides a method for manufacturing of an influenza vaccine which induces an increased cross-reactive immune response and cross protection. The method comprises treating an influenza antigen comprising the HA at a suitable low pH and temperature. The treated antigen obtains a suitable degree of loss of potency. The treated antigen is then formulated as a vaccine with pharmaceutically acceptable carriers. The vaccine can be further formulated to meet the potency standard by compensating the partial potency loss of the treated antigen with additional antigens or an adjuvant. The resulting vaccine will then further induce the strain-specific immune responses and protection like current inactivated vaccines.

The present invention further provides a method of administering an influenza vaccine for induction of an increased cross-reactive immune response and cross protection. The method comprises treating a vaccine comprising an influenza HA-containing antigen at a suitable low pH to generate a suitable degree of loss of potency and then administrating the treated vaccine to an animal or human. The low pH treatment may be performed using a kit containing required acidic and basic solutions. This method can be used to convert existing vaccines in circulation or stockpiles to provide an increased cross protection in emergency situations such as a pandemic. It could be a critically important countermeasure in the possible pandemic scenario in which stockpiled vaccines are not a direct match to the pandemic virus and vaccines specific to the pandemic virus are not available or in short supplies.

BRIEF DESCRIPTION OF THE DRAWINGS

Figure 6:
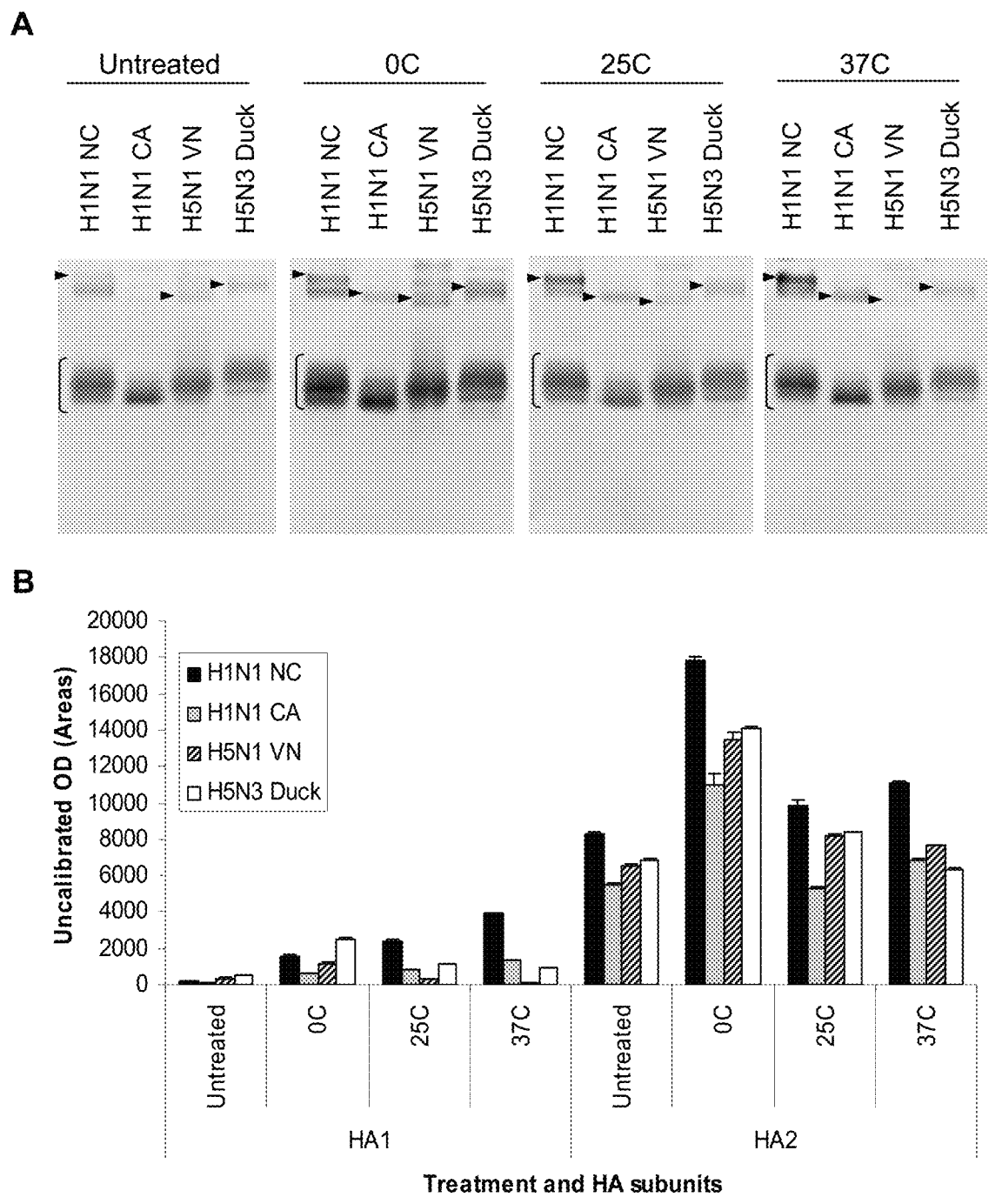

FIG. 6 shows the increased antibody reaction with HA1 and HA2 induced by low pH-treated antigens. The same pooled serum samples against the untreated or low pH-treated (pH5.1 at 0, 25, or 37° C.) inactivated WV antigen (A/New Caledonia/20/99, H1N1 NC) as in FIG. 3 were tested with the homologous (H1N1 NC) and different heterologous antigens (H1N1 CA, H5N1 VN, and H5N3 duck) by immunoblot. Panel A shows the immunoblot. Panel B shows the plot of densities (uncalibrated OD) of HA1 and HA2 protein bands in the immunoblot of panel A. Arrow heads indicate the HA1 and brackets indicate the HA2.

DETAILED DESCRIPTION OF THE INVENTION

Definitions

Figure 1:
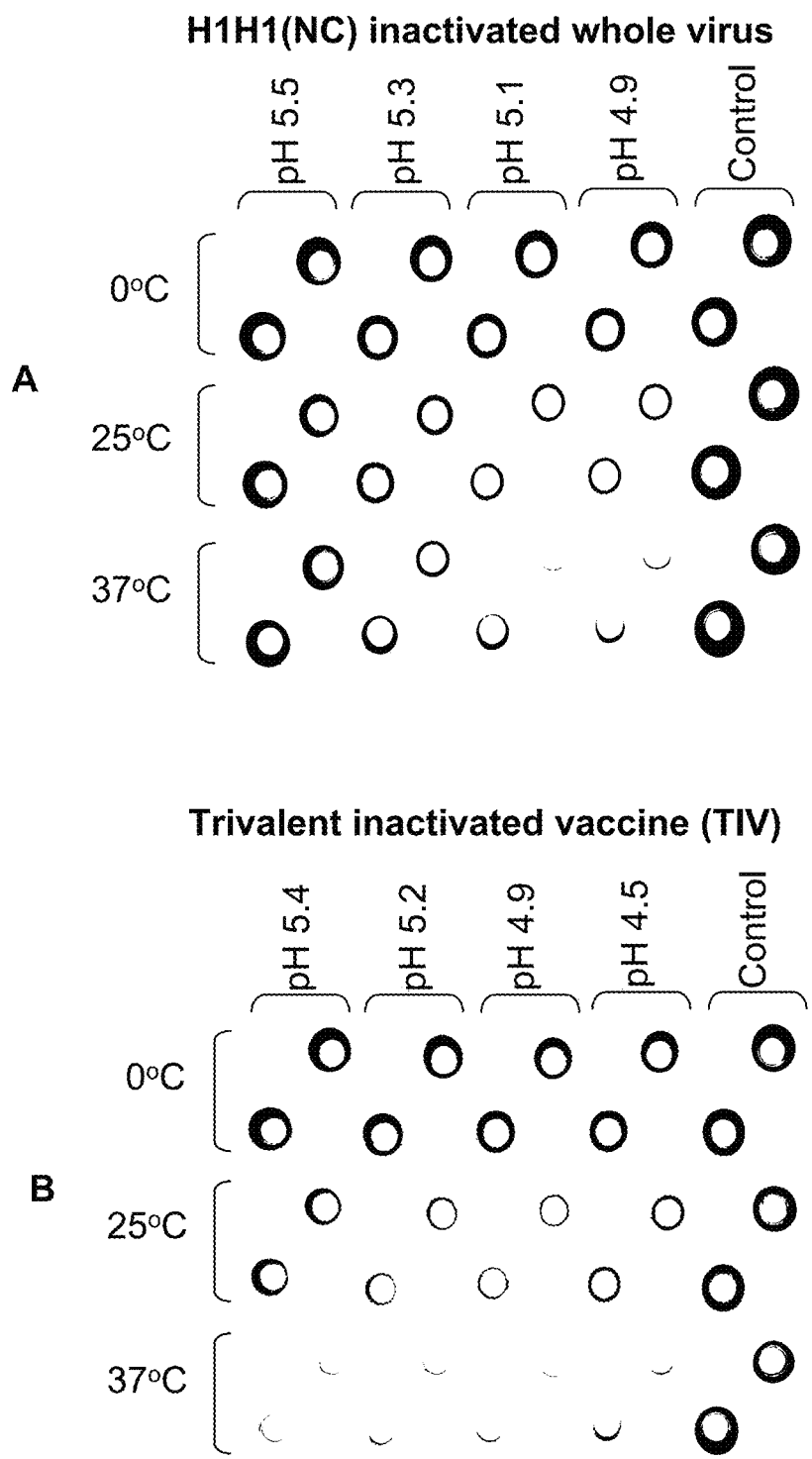
FIG. 1 shows the single radial diffusion (SRD) test with inactivated WV antigen (A/New Caledonia/20/99, H1N1 NC) (A) and TIV (2006-2007, Fluzone) (B) following treatment at different pHs and temperatures.
Figure 2:
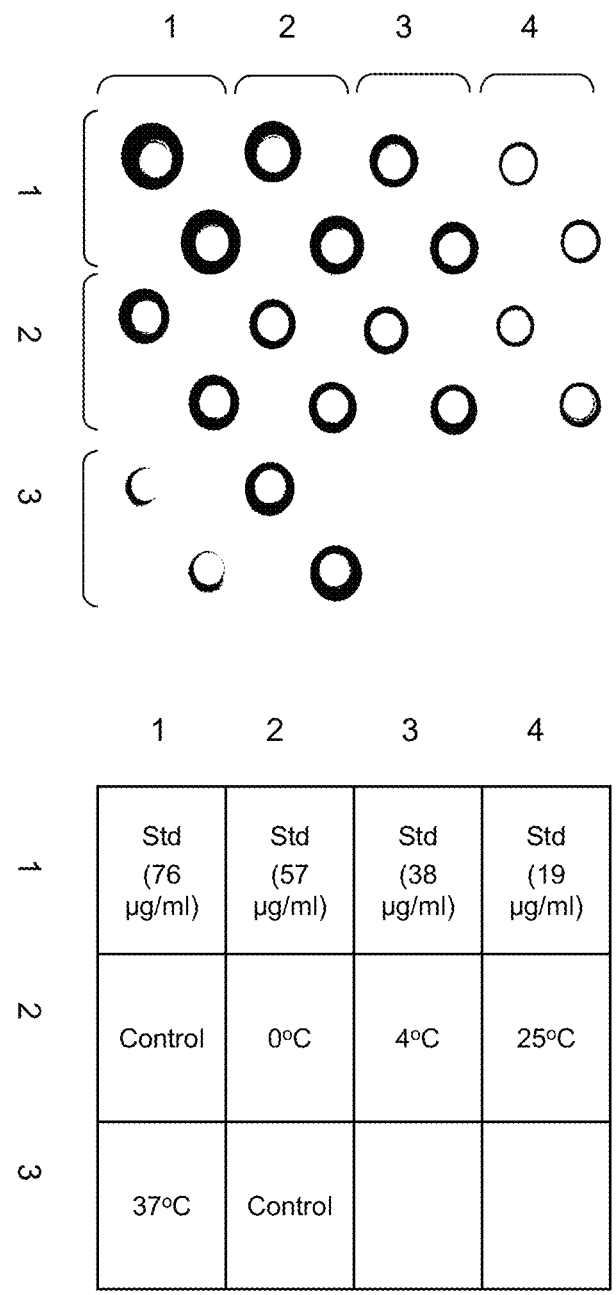
FIG. 2 shows the single radial diffusion (SRD) test with inactivated WV antigen (A/New Caledonia/20/99, H1N1 NC) following treatment at pH 5.1 and different temperatures along with the reference antigen standard (std) with known HA concentrations (μg/ml).

The words "antigen" and "immunogen" are used interchangeably and refer to a molecule, a substance, a protein, a glycoprotein, or a live virus that can induce specific humoral (antibody) and cellular immune responses.

The word "antigenicity" used herein refers to the ability of an antigen to react or bind with specific antibodies.

The word "immunogenicity" used herein refers to the ability of an antigen or vaccine to induce specific immune responses.

The term "immune response" refers to humoral or antibody-mediated and cell-mediated immune responses against an antigen, vaccine or infectious agent.

The word "vaccine" refers to a composition comprising an antigen for therapeutic treatment of or prophylactic immunization against an infectious or non-infectious disease.

The word "immunity" refers to immune responses generated by vaccination or infection which provide protection against an infectious or foreign agent.

The term "recombinant protein or antigen" refers to protein or antigen produced with recombinant DNA techniques which can be used to clone and express genes to produce proteins in various hosts including bacteria, mammalian cells, insect cells, and plants. The recombinant DNA techniques are described in numerous published books and manuals, including "Current protocols in molecular biology" (Ausubel eds. 2008. John Wiley & Son). The recombinant protein or antigen may exist as individual proteins or a complex such as virus-like particles.

The word "disease" or term "disease condition" refers to any abnormal change in an animal or human that may be caused by an infectious agent or other underlying mechanisms. It is used interchangeably with "illness".

The term "infectious agent" and "pathogen" are used interchangeably and refer to an infectious microorganism such as a virus or bacterium as well as disease causing agents such as toxins of various origins.

The word "a" or "an" means "one or more".

The words "inactivated" and "inactivation" refers to killing or rendering live viruses non-infectious or non-living during production of an inactivated vaccine from live viruses. The inactivation may be performed at different stages of the vaccine production process, e.g., before or after virus purification. The "inactivated" is also used interchangeably with the "non-living". The non-living vaccines may also include antigens produced by recombinant DNA techniques such as recombinant HA and virus-like particles.

The term "low pH" is used interchangeably with acidic pH. It refers to a pH less than 7.0.

The word "potency" refers to the amount of an antigen in an antigen preparation or vaccine as measured by a designated potency assay. For vaccines, a required level or standard of the potency must be met, which is directly correlated with efficacy or effectiveness of the vaccine. For current inactivated or non-living influenza vaccines, the potency is the amount of HA protein measured by the designated SRD test. It is strain-specific as the SRD is conducted with polyclonal antibodies generated specifically against the HA of the virus strain to be tested and used in the vaccine. The potency standard for a vaccine could vary due to several factors including antigen types, populations for the intended use, and use of adjuvant.

The terms "loss of potency", "potency loss", and "reduction in potency" are used interchangeably and refer to a decrease in potency of an antigen or vaccine as measured by the potency test. The loss of potency reflects the antigenic or structural changes of an antigen or vaccine. Besides the potency test, these changes may be measured by a functionally equivalent alternative method.

The term "homologous virus or antigen" refers to an influenza virus or antigen that is serologically similar to others in a group within a subtype as commonly defined by HAI test based on the well established criteria (generally considered as a difference of ≤4 fold in HAI titer).

The term "heterologous virus or antigen" refers to an influenza virus or antigen which is serologically different from others of either the same or a different subtype as commonly defined by HAI test based on the well established criteria (generally considered as a difference of ≥8 fold in HAI titer). It is used interchangeably with "variant virus or antigen".

The term "cross-reactive" refers to that the immune response generated by an antigen, vaccine or virus is reactive with a heterologous virus or antigen.

The term "cross protection" refers to that the protection generated in a host by an antigen, vaccine, or infection against one virus prevents infection or disease caused by a heterologous virus.

DETAILED DESCRIPTION

The first aspect of the present invention is that the potency of influenza antigens comprising HA can be gradually reduced by up to 100% by low pH treatment in direct correlation with treatment conditions. Thus, the lower the pH, the higher the potency loss. Increasing temperature drastically enhances the effect of low pH in reducing the potency. As shown in Examples 1, 2, and 4, a treatment at a pH of 5.1 or 5.2 and 37° C. resulted in a potency loss by ≥90%, whereas treatment at the same pH and 0 or 4° C. reduced the potency by <50%. A potency loss as low as ~10% was obtained when low pH treatment was 30 performed at pH 5.2 and 0° C. This effect of low pH on potency was demonstrated with inactivated WV antigens, TIV as well as recombinant HA. The loss of potency is irreversible as the SRD test was performed after adjusting pH back to the original level (7.0-7.4) following low pH treatment. The extent of potency loss could vary with different antigens under the same condition. But the same level of potency loss with different antigens or vaccines can be readily obtained by adjusting treatment conditions.

The second aspect of the present invention is that the low pH-treated antigens can induce increased cross-reactive antibody responses against heterologous antigens when administered to animals in correlation with the potency loss. As shown in Examples 3 and 4, all treated antigens induced the increased cross reaction with heterologous antigens as measured by ELISA for total specific antibodies. The ones treated at the more stringent condition (pH 5.1 or 5.2 and 37° C.) with a potency loss of ≥90% induced the highest cross reaction. However, antigens treated at the mild condition (pH 5.1 or 5.2 and 0-25° C.) with a potency loss of <50% and as low as 12.5% also induced strong cross reaction. Such increased cross-reactive antibody response was not only demonstrated with the inactivated antigens, but also the recombinant HA proteins, indicating that the increased cross-reactive antibody response is directed toward HA. The level of the increased cross reaction appears to be higher with heterologous antigens from the same phylogenetic group. This is consistent with the fact that the two phylogenetic groups are established based on the sequence homology of the HA proteins.

The third aspect of the present invention is that antigens treated at appropriate low pH conditions with a partial potency loss can induce greater cross reaction with HA2, the highly conserved part of HA. As shown in Examples 3 and 4 by immunoblot, antigens treated under different low pH conditions (pH 5.1 or 5.2 and 0, 25, or 37° C.) induced increased reactions with both HA1 and HA2, but remarkably, with distinctly different patterns. The antigen treated at the mild conditions (0-25° C.) induced the greater reaction with HA2, whereas the one treated at the more stringent condition (37° C.) induced the greater reaction with HA1. This indicates that antigenic or structural changes induced under different treatment conditions are not only quantitative, but also qualitative. In Examples 3 and 4, the largest increase in reaction with HA2 was obtained with antigens treated at the mild conditions with a potency loss within the range of 20-50%. Importantly, it occurred consistently with all heterologous antigens tested. Thus, a certain range of the potency loss obtained under the appropriate treatment conditions is particularly effective in inducing the increased cross reaction with HA2. On the other hand, the levels of the increased cross reaction with HA1 of heterologous antigens varied between individual antigens under different conditions. These results are consistent with the fact that HA2 is much more conserved than HA1. Similar to the findings by ELISA described above, the cross reaction with HA2 also appears to be higher with heterologous antigens from the same phylogenetic group.

The HAI and NT measure the neutralizing antibodies. The untreated antigen (A/New Caledonia/20/99) induces high HAI and NT titers against the homologous virus, but no detectable HAI or NT titers against a heterologous virus (A/Puerto Rico/8/34, H1N1 PR8) as expected. The treated antigens induced lower HAI and NT titers against the homologous virus in correlation with the potency loss. However, the antigens treated at the mild condition (0-25° C.) with a potency loss of <50% are still capable of inducing substantial HAI and NT titers which are either at the same level or only lower by ~2 fold as compared to the untreated antigen. Importantly, certain treated antigens obtained under the mild conditions (pH 5.2 and 25° C.) are also capable of inducing a low and yet increased level of HAI and NT titers against the heterologous virus as shown in Example 4.

The fourth aspect of the present invention is that the same treated antigens obtained at appropriate low pH conditions with a partial potency loss can induce an increased cross protection. The Example 4 showed that antigens treated at mild conditions (0 or 25° C.) with a partial potency loss of <50% induced the increased cross protection. In contrast and unexpectedly, the antigen treated at 37° C. with a potency loss of >90% did not provide any detectable cross protection under the experimental conditions used, although high levels of total cross-reactive antibody response and cross reaction with HA1 was induced by this antigen. It is therefore clear that the increased cross protection is correlated with the partial potency loss (<50%) and the increased cross reaction with HA2. Quan et al (Virology. 417:196-202, 2011) evaluated inactivated WV antigens treated at low pH (5.0) and 37° C. in an effort to generate cross-reactive immune response and cross protection based on the understanding of the known effect of low pH on conformational changes of HA. However, the treated antigen lost the hemagglutination activity by 24 fold and did not induce any increased cross-reactive antibody responses, nor any increased cross protection against heterologous viruses. It actually was less effective than the untreated antigen in inducing the cross-reactive antibody responses and cross protection (Quan et al., Virology. 417:196-202, 2011). This is consistent with the results with the antigen treated at 37° C. in the present invention with respect to lack of an increased cross protection, and further indicated the unexpected nature of the current invention that it is the antigens treated at mild low pH conditions with a partial potency loss that induced the increased cross-reactive immune responses and cross protection. Although not wanting to be bound by the theory, it is possible that antigens treated at mild conditions may have only gained limited antigenic or structural changes which are suited for better exposure of HA2 and possibly other conserved domains in their native forms and consequently increase cross reaction and protection, whereas those treated at 37° C. may have gained excessive antigenic or structural changes as evidenced by the nearly complete potency loss and therefore may be less relevant to the native HA and consequently less protective, even when increased immune responses are induced against them.

The effect of low pH on HA of influenza viruses has been studied extensively (Skehel and Wiley, Annu. Rev. Biochem. 69:531-569, 2000; Luo, Adv Exp Med Biol. 726:201-221, 2012). However, no studies have previously focused on the effect of low pH on potency of influenza antigens and vaccines and induction of increased cross-reactive immune responses and cross protection with antigens treated under different low pH conditions. Thus, the present invention first showed that the potency of influenza antigens can be reduced by up to 100% in correlation with low pH treatment conditions. The current invention further demonstrated that only the antigens with a suitable degree of potency loss obtained under appropriate low pH treatment conditions induce a greater cross reaction with HA2, the highly conserved part of HA, and an increased cross protection. Together, these discoveries formed the basis for new and improved influenza vaccines based on antigens treated under suitable low pH conditions.

One embodiment of the present invention is an influenza vaccine comprising an influenza antigen treated at a suitable low pH condition with a partial potency loss, which induces an increased cross-reactive response and cross protection. It is preferred that the treated antigen retains its original hemagglutination activity following the low pH treatment. The vaccine can be formulated with an adjuvant to further enhance the cross-reactive immune responses and cross protection.

Another embodiment of the present invention is an influenza vaccine comprising an influenza antigen treated at a suitable low pH condition with a partial potency loss, which not only provides an increased cross-reactive immune response and cross protection, but also meets the potency standards, thereby providing the same level of strain-specific protection against influenza viruses contained in the vaccine as with the untreated antigen or like current inactivated vaccines. This dual-effect vaccine can be made by compensating the partial potency loss of the treated antigen through incorporating a suitable amount of additional antigens or an adjuvant as described in Example 6.

It is known that the strain-specific immune responses and protection is mainly mediated through HA1, the immunodominant part of HA in the current inactivated vaccines. The strain-specific protection is primarily conferred by neutralizing antibodies as measured by HAI and NT. According to the current invention, the increased cross-reactive antibody responses and cross protection induced by antigens treated at suitable low pH conditions is associated with the increased reaction with HA2. Thus, this dual-effect vaccine makes a balanced use of HA1 and HA2, the former for primarily inducing strain-specific immune responses and protection and the latter for primarily inducing the increased cross-reactive immune responses and cross protection. Both neutralizing and non-neutralizing antibodies can be involved in the cross protection induced by antigens treated at suitable low pH conditions. As described above, the non-neutralizing antibodies can also be highly protective.

Influenza vaccines according to the present invention can be made with single or multiple antigens. In the case of multiple antigens, either a part or all of the antigens may be treated at low pH conditions suitable for the respective antigens. Current TIV contains antigens from three virus strains, H1N1, H3N2, and B. Recently, a quadrivalent inactivated vaccine (QIV) has been licensed, which is same as TIV, but incorporates an additional B virus. The H1 subtype belongs to phylogenetic group I, whereas H3 subtype belongs to phylogenetic group II. Thus, if treated antigens from both H1 and H3 subtypes are incorporated, even broader cross-reactive antibody responses and cross protection can be generated. This is particularly advantageous considering that the two phylogenetic groups are established based on the sequence homology of HA proteins, and therefore the level of cross reaction is expected to be higher with viruses within the same phylogenetic group. These antigens are therefore highly suitable for making a new generation of TIV or QIV based on the current inventions. Such new vaccines will not only fulfill its original indication—the strain-specific protection against viruses contained in the vaccine, but can also provide an increased cross protection against other viruses not contained in the vaccine, including possible pandemic as well as seasonal variant viruses. A very distinct advantage of this new broad-spectrum TIV or QIV is that it can be readily incorporated into the current immunization programs against influenza. This new TIV or QIV can further incorporate treated antigens from additional clades to become a multivalent or multiclade vaccine comprising antigens from two or more clades of one phylogenetic group and at least one clade from the other phylogenetic group. Antigens from all five current clades of the two phylogenetic groups may be incorporated into this multiclade vaccine. The resulting vaccines will further enhance and broaden cross-reactive immune responses and cross protection by further strengthening the cross reactivity within and between clades and phylogenetic groups through the more conserved HA2 as the result of use of antigens treated under the appropriate low pH conditions. Such vaccines possess the capability to provide the antigenic breadth sufficient for reaching the ultimate goal of achieving true universal protection.

Still, another embodiment of the present invention is a method to produce influenza vaccines which induce an increased cross-reactive immune response and cross protection. Thus, influenza antigens comprising HA are treated at a suitable low pH condition to obtain a desired level of potency loss for induction of increased cross-reactive immune responses and cross protection. For low pH treatment, an acidic pH solution may be added to the antigen to adjust the pH to a suitable low pH level, the antigen is then kept at a suitable temperature for a suitable period of time, and the pH of the antigen is adjusted back to the original or physiological level (7.0-7.4) at the end of the treatment. Specific treatment conditions may vary with different antigens based on the antigen form, virus strain, source, and method of production. Suitable conditions for a given antigen can be established by testing under a wide range of pH and temperature. The low pH treatment may be performed at any stages of the manufacturing process such as bulk antigens before they are formulated into final vaccine products. For inactivated antigens made from live viruses grown in chicken eggs or cultured avian or mammalian cells, the low pH treatment may be performed either before or after the inactivation. The inactivated antigens may be further fixed with formaldehyde or other suitable agents after low-pH treatment to ensure the long term stability of the antigen. The low pH treatment may be preferably performed at 2-8° C. or below room temperature to maintain the antigen stability and minimize the chance of microbial contamination. For multivalent vaccines, individual antigens may be treated separately under different suitable conditions before being combined to make the final vaccine. The final vaccine may be formulated to meet the potency standard by compensating the partial potency loss of treated antigens through incorporating a suitable amount of additional untreated or treated antigens or a suitable adjuvant as described in Example 6. For treated antigens with a very low potency loss, the antigen compensation may not be necessary as such antigens may be still capable of inducing the same level of strain-specific immune responses.

Another embodiment of the present invention is a method for administering an influenza vaccine to an animal or human to induce an increased cross-reactive immune response and cross protection. Thus, an acidic solution or a low pH buffered solution (treating solution) is added to the vaccine to lower the pH of the vaccine to a suitable level such as 5.0-6.0. The vaccine is then kept at a suitable temperature (4, 25, or 37° C.) for a suitable period of time to induce a suitable level of potency loss. A basic solution or high pH buffer (stopping solution) is added to stop the treatment by bringing the pH back to its original or physiological level (7.0-7.4). The vaccine is then administered to an animal or human. The step for addition of the basic solution is optional as the pH of the vaccine mixed with the acidic solution may be quickly changed to the physiological level upon contacting the body fluids. A kit comprising an acidic solution and a basic solution can be provided to facilitate the treatment of vaccines in either multi-dose vials or single-dose syringes. This method is especially important in possible pandemic scenarios in which existing vaccines in circulation or stockpiles are not a direct match to the pandemic virus and the vaccines specific to the pandemic virus are not available or in short supplies. Thus, these existing vaccines can be converted by low pH treatment under proper condition just prior to administration to provide an increased cross protection, which otherwise will be less or not effective. Considering the current limited global vaccine production capacity, the shortage of the pandemic vaccine is inevitable, especially during the early stage of a pandemic. Thus, low pH treatment of existing vaccines under proper low conditions could provide an effective counter measure in case of such an emergency scenario.

Any antigens or vaccines comprising HA may be suitable for use by the present invention. They may be produced by various manufacturing systems such as bacterial cells, avian cells, mammalian cells, chicken eggs, insect cells, plant cells, insects, and plants. They may also be in different forms such as WV, split virus, subunit, virosome, recombinant HA and virus-like particles. They can be inactivated antigens produced from live viruses or recombinant proteins produced by recombinant DNA techniques. The HA in the antigen may be a part of or whole HA molecule and may also be modified by insertion, deletion, and/or substitution of one or more amino acids by recombinant DNA techniques. The recombinant HA may be optionally treated with proteases to remove the covalent linkage between HA1 and HA2 prior to the low pH treatment (Wang et al., Vaccine. 24:2176-2185, 2006).

For practicing the current invention, antigens may be treated at a suitable low pH ranging from 3.0 to 6.8 and a temperature of 0° C. or higher. The suitable low pH treatment conditions may vary with different antigens based on the strain, form, source, and method of production. Thus, for a given antigen, the suitable treatment condition may be identified by screening a wide range of low pHs (3-6.9) at different temperatures (0-37° C.) based on the desired level or range of potency loss for induction of cross-reactive immune responses and cross protection. The antigens may risk to be denatured at a very low pH (<4.5), making them antigenically less relevant to influenza virus. Thus, the low pH treatment may be preferably performed at pH 4.5-6.5 and an appropriate temperature to achieve a desired level of potency loss, while minimizing any possible denaturing of the antigen. Since the effect of low pH on potency is enhanced by increasing temperature, it is possible that a same level of potency loss can be reached under different conditions based on combination of the specific low pH and temperature used.

The extent of potency loss suitable for induction of an increased cross-reactive immune response and cross protection can vary with different antigens, which may range from 1-100%. As evidenced in Examples 3 and 4, potency losses within a certain range (20-50%) induced the highest cross reaction with HA2 with the H1N1 NC WV antigen. However, the suitable range of potency loss may vary with different antigens. The potency loss of about 50% or less is preferred since antigens with such a partial potency loss can be particularly effective in inducing the increased cross-reactive immune responses and cross protection, and at the same time are also capable of inducing a substantial or the same level of strain-specific immune responses. They can be formulated to meet the potency standard with less additional antigens. Antigens with a potency loss of only 12.5% can be effective as shown in Example 4. The temperature in the range of 0-25° C. is preferred for generation of treated antigens with relatively lower potency loss (about 50% or less). Since vaccines are produced and stored at a cold temperature (2-8° C.) for the purposes of vaccine stability and prevention of microbial contamination, the temperature in the range of 2-8° C. can be particularly suitable.

It is preferred that the hemagglutination activity of the antigens is preserved after the low pH treatment. Thus, the hemagglutination titer preferably remains the same or has a <2 fold reduction after the low pH treatment. The hemagglutination activity reflects the binding of the HA to the cellular receptor and is an important indicator for stability. An alternative method for measuring the binding of the HA to the receptor may be used. It is understood that some antigens or vaccines may not have the hemagglutination activity depending on the production methods used. Thus, hemagglutination activity may not be available to assess some of the treated antigens or vaccines.

The agents used to adjust pH during low pH treatment can be simple acids and bases. The acid for lowering the pH can be selected from a group comprising hydrochloric acid (HCl), acetic acid, citric acid, boric acid, MES (2-(N-morpholino) ethanesulfonic acid), and phosphoric acid. The base for raising the pH to a physiological level after the low pH treatment can be selected from a group comprising sodium hydroxide (NaOH), sodium acetate, sodium citrate, sodium borate, sodium phosphate, and Tris (tris(hydroxymethyl)aminomethane). They can be made as sterile solutions for mixing with antigens or vaccines. Alternatively, a low pH buffer made with these acids and bases, e.g. a citrate or acetate buffer at a suitable low pH, may be used to lower the pH, and a basic pH buffer, e.g., a citrate, Tris, or phosphate buffer at ~pH 8.0, may be used to raise the pH back to the original or physiological pH level (7.0-7.4). The use of buffers has an advantage of minimizing the chance of exposing the antigen to an extreme pH.

The suitable range of potency loss of the antigens for increasing cross-reactive immune responses and cross protection may be obtained by treatment at other suitable conditions. It is known that a treatment at high temperatures or with denaturing agents such as urea can induce similar conformational changes of the HA protein like low pH (Carr et al., 1997). Thus, alternative treatment conditions based on a denaturing agent like urea, high temperature or other chemical and physical means may also be used to produce treated antigens with a suitable range of potency loss for induction of increased cross-reactive immune responses and cross protection according to the current invention. As an example, a gradual reduction of potency could be obtained by treatment at different high temperatures (50-68° C.; Example 8). A suitable range of high temperatures for antigen treatment may range from 40 to 80° C., considering that the suitable temperature may vary with different antigens. To avoid possible denaturing of the antigen, a lower temperature range of 37-70° C. may be preferred. The effect of temperature is time-dependent. A suitable degree of loss of potency may be obtained by treatment for a longer time at lower temperatures which may include 37° C. or lower. The hemagglutination activity of the antigen is also preferably preserved after the high temperature or other alternative treatments.

The potency loss reflects antigenic or structural changes of the HA molecule. The SRD is performed with polyclonal antibodies specific to the HA. The polyclonal antibodies consist of individual antibodies recognizing various different epitopes on the HA molecule which can be conformational or linear as a structure made of discontinuous parts or a linear stretch of the primary amino acid sequence. A reduction in potency therefore reflects antigenic or structural changes in certain areas of the molecule, eliminating some of the original epitopes and exposing previously less exposed or hidden ones. The loss of potency is the preferred indicator for the antigenic or structural changes after the low pH treatment as it is directly related to the ability of the antigen or vaccine to induce increased cross-reactive immune response and protein as well as strain-specific immune responses and protection. However, the loss of potency may be correlated with a functionally equivalent alternative measurement for antigenic or structural changes for a part of or whole HA, which may include a biological, immunological, chemical, biochemical, or morphological method such as reaction with monoclonal antibodies, protease sensitivity, hemolysis, cell fusion, electron microscopy, differential scanning calorimetry (DSC) and circular dichroism (CD). Thus, the antigenic or structural changes may be indicated and monitored by a functionally equivalent alternative measurement during the low pH treatment, and the potency of treated antigens is determined later for formulation of the final vaccine to meet the potency standard. As an example, the protease sensitivity can be correlated with the potency loss (Example 5). In the future, a new potency assay may be developed for influenza vaccines to correlate with and replace the current SRD test.

The vaccines according to current invention may be formulated with various different pharmaceutical excipients or carriers. They may include salts and buffers to provide a physiological ionic strength and pH, a surfactant such as polysorbate 20 and 80 to prevent antigen aggregation, a stabilizing agent for antigen stabilization such as PEG, trehalose, and gelatin, and a polymer for sustained release such as CMC, HEC, and dextran. The vaccine may also be formulated with a controlled release or enhanced presentation system such as hydrogel, virosome, nanoparticle, and emulsion. The vaccine may also be formulated with an adjuvant to further increase the cross-reactive immune responses and cross protection, which may include those described in Example 6. The vaccine may be administered by various routes such as intramuscular, subcutaneous, intranasal, topical, sublingual, or oral.

In summary, the current invention provides a new and improved influenza vaccine and the methods for producing and administering it. The vaccine can not only provide an increased cross-reactive immune response and cross protection against heterologous viruses, but also the strain-specific protection against seasonal influenza viruses like current inactivated vaccines. It thus possesses distinct advantages in meeting the urgent need to provide protection against possible future pandemics as well as better control of seasonal influenza epidemics. The following examples are provided to illustrate the principle of the current invention without limiting its scope.

Example 1

Potency of Inactivated Influenza Whole Virus (WV) Antigens Following Low pH Treatment Inactivated WV antigens from three virus strains (A/New Caledonia/20/99, H1H1 (H1N1 NC); A/Wisconsin/67/2005, H3N2 (H3N2 Wis); B/Malaysia/2506/2004 (B Mal) were used. They were produced by purification from infected MDCK cells and inactivation with formaldehyde (1/4000 dilution or 0.01%) for at least three days at 4° C. The inactivation was confirmed by titration in chicken eggs and plaque assay in MDCK cells.

For low pH treatment, antigens in phosphate buffered saline (PBS, pH7.2; ~2.0 mg/ml) were diluted 1:10 with 20 mM sodium citrate buffers containing 150 mM NaCl (pH 4.6-5.4 in 0.2 increments) to bring the pH of antigens to 4.9-5.5 with a final antigen concentration at 0.2 mg/ml. The antigens were then kept at 0° C. (on ice), 4° C., 25° C. (room temperature), or 37° C. for 15 min before the pH was adjusted with an appropriate volume of 1 M Tris HCl buffer (pH8.0) back to the original level (7.0-7.4). Alternatively, low pH buffers (0.2M Citrate/0.1M phosphate, pH 3.6-6.6 in 0.2 increments) were used by dilution with antigen (e.g., 1:10). This allows the antigens to be treated at a higher protein concentration. The potency or the amount of HA of inactivated antigens was measured by SRD test according to the procedure described by Wood et al. (J Biol Stand. 5:237-247, 1977; Dev Biol Stand. 64:169-177, 1986). The SRD reference sera and antigens (H1N1, H3N2, and B; FDA) were used at the recommended concentrations provided in the instructions.

For screening of different conditions, the results were analyzed based on the sizes of precipitation rings formed in the SRD test plates. They showed that low pH-treated antigens exhibited a reduced potency as reflected by smaller precipitation rings (FIG. 1A and Table 1). The reduction in the precipitation ring size or potency was directly correlated with the treatment conditions. The lower the pH, the larger the potency loss (FIG. 1A and Table 1). Increasing temperature drastically enhanced the effect of low pH in reducing the potency (FIG. 1A and Table 1). A full range of potency loss (17.6-98.6%) was obtained with treatment conditions from the mildest (pH 5.5 and 0° C.) to the most stringent (pH4.9 and 37° C.). The FIG. 2 shows the potency of H1N1 WV antigens treated at pH 5.1 and different temperatures along with the reference standard. No apparent difference in potency loss was observed between 0 and 4° C.

Similar results were obtained with inactivated H3N2 and B WV antigens, i.e., the potency loss increased along with decrease in pH and increase in temperature. However, the extent of potency loss varied among different antigens. The H3N2 antigen showed a similar extent of potency loss with the H1N1 antigen under various conditions, whereas the B antigen was much more sensitive to the low pH treatment—a >50% potency loss was obtained at 4° C. and pH5.6.

Following low pH treatment, hemagglutination activity was also measured using 1% chicken red blood cells (RBC) in 96-well V-bottom plates. The antigens were serially diluted by 2 fold in 50 μl PBS in duplicate and then mixed with equal volume of 1% fresh chicken RBC. The plates were kept at room temperature for 1 hr before hemagglutination titer was determined, which was the highest dilution with complete agglutination. The results showed that for H1N1 NC antigen, the hemagglutination activity remained the same when potency was lost by 93.1% and only decreased by 2 fold after treatment at the lowest pH (4.9) and 37° C. with a 98.6% potency loss (Table 2).

TABLE 1

Potency of inactivated WV antigens (H1N1, NC) as indicated by precipitation ring sizes following the low pH treatment.

| | Precipitation ring size ($mm^2$)* (% reduction) | | | | |
|---|---|---|---|---|---|
| | | pH | | | |
| Temperature | Control | 4.9 | 5.1 | 5.3 | 5.5 |
| 0° C. | 27.5 (0%) | 17.9 (34.9%) | 20.6 (25.1%) | 19.4 (29.6%) | 22.7 (17.6%) |
| 25° C. | 32.7 (0%) | 6.1 (81.3%) | 7.8 (76.0%) | 13.7 (58%) | 20.4 (37.6%) |
| 37° C. | 32.4 (0%) | 0.5 (98.6%) | 2.2 (93.1%) | 7.8 (75.8%) | 19.4 (40.1%) |

*Excluding the area of the center well.

TABLE 2

Hemagglutination activity of inactivated WV antigens (H1N1, NC) following the low pH treatment.

| Temperature | Control | pH 4.9 | pH 5.1 | pH 5.3 | pH 5.5 |
|---|---|---|---|---|---|
| 0° C. | 1600 | 1600 | 1600 | 1600 | 1600 |
| 25° C. | 1600 | 1600 | 1600 | 1600 | 1600 |
| 37° C. | 1600 | 800 | 1600 | 1600 | 1600 |

Example 2

Potency of Trivalent Inactivated Vaccine (TIV) Following Low pH Treatment

A TIV (Fluzone, 2006-2007) which contains the antigens from the same three virus strains described in Example 1 was also evaluated for potency after low pH treatment under different conditions. The vaccine was similarly treated, but with appropriate volumes of 0.1 M HCl added to the vaccine to adjust the pH to a similar range before neutralization with an equal volume of 0.1 M NaOH. The potency of H1N1 NC strain was measured. The results were similar to those obtained with inactivated WV antigens as described above (FIG. 1B and Table 3). However, TIV was more susceptible to low pH treatment than the WV antigen in that at any given condition, potency loss was greater with TIV. This may be related to the fact that TIV is made of split antigens. A complete potency loss (100%) was obtained at 37° C. for all pH levels tested (FIG. 1B and Table 3). Similarly, hemagglutination activity only decreased by 2 fold or more after treatment at 37° C. or the lowest pH (4.5) (Table 4).

In a separate test, the vaccine was treated at pH 5.2 and four different temperatures (0, 4, 25, or 37° C.) with potency for all three strains tested. The H1 and H3 antigens exhibited similar levels of potency loss under different conditions, whereas the B antigen showed a much greater loss, being consistent with results using inactivated WV antigens (Example 1). No difference in potency loss was observed between 0 and 4° C.

TABLE 3

Potency of trivalent inactivated vaccine for the H1N1 (NC) strain as indicated by precipitation ring sizes following the low pH treatment.

Precipitation ring size (mm²)* (% reduction)

| Temperature | Control | pH 4.5 | pH 4.9 | pH 5.2 | pH 5.4 |
|---|---|---|---|---|---|
| 0° C. | 23.5 (0%) | 14.2 (39.6%) | 13.3 (43.4%) | 13.9 (40.5%) | 15.5 (33.7%) |
| 25° C. | 22.4 (0%) | 4.8 (78.5%) | 0.0 (100%) | 0.0 (100%) | 7.6 (65.9%) |
| 37° C. | 21.6 (0%) | 0.0 (100%) | 0.0 (100%) | 0.0 (100%) | 0.0 (100%) |

*Excluding the area of the center well.

TABLE 4

Hemagglutination activity of trivalent inactivated vaccine following the low pH treatment.

| Temperature | Control | pH 4.5 | pH 4.9 | pH 5.2 | pH 5.4 |
|---|---|---|---|---|---|
| 0° C. | 3200 | 3200 | 3200 | 3200 | 3200 |
| 25° C. | 3200 | 1600 | 3200 | 3200 | 3200 |
| 37° C. | 3200 | 800 | 800 | 800 | 800 |

Example 3

Induction of Increased Cross-Reactive Antibody Responses by Low pH-Treated Antigens Low pH-treated H1N1 NC WV antigens with different levels of potency loss were used to immunize 6-8 weeks old female Balb/c mice (n=7) together with the untreated control. The antigens were treated at pH 5.1 and different temperatures (0, 25, and 37° C.) and the potency (HA. µg/ml) was determined as described in Example 1. The treated antigens exhibited the potency reduction in correlation with the treatment conditions, but retained the original hemagglutination activity (Table 5).

Mice were immunized at the same antigen dose based on total proteins which was equivalent to 1 µg HA/mouse for untreated antigen by intramuscular injection twice, 4 weeks apart. A group receiving a mixture of antigens containing equal parts of the untreated antigen and the one treated at 37° C. was also included (Table 5). The mixed antigen exhibited a similar level of potency as the untreated antigen as expected (Table 5). Serum samples were collected every two weeks till week 4 after the $2^{nd}$ immunization. Specific antibodies were measured by hemagglutination inhibition (HAI), neutralization test (NT), ELISA, and immunoblot.

TABLE 5

Potency and hemagglutination titers of inactivated
WV antigens (H1N1 NC) after low pH (5.1) treatment.

| Antigens | Total protein (μg/ml) | Potency (HA μg/ml; % reduction) | Hemagglutination |
|---|---|---|---|
| Untreated | 220 | 50.7 (0%) | 1600 |
| 0° C. | 220 | 40 (21.1%) | 1600 |
| 25° C. | 220 | 17.1 (66.3%) | 1600 |
| 37° C. | 220 | 5.6 (90%) | 1600 |
| Mix | 440 | 56.3 (N/A) | N/A |

HAI and NT

HAI and NT measure the neutralizing antibodies. HAI test was performed using chicken RBC as described in WHO manual on animal influenza diagnosis and surveillance (WHO/CDS/CSR/NCS/2002.5). Briefly, individual or pooled serum samples were treated with receptor destroying enzyme (RDE) at 37° C. overnight and then inactivated at 56° C. for 30 min before being used in HAI test. The HAI titer was the highest dilution with complete inhibition of agglutination (streaming down of RBC dots when the plate is tilted).

NT was performed in MDCK cells in 96-well plates. Pooled serum samples from each group were inactivated at 56° C. for 30 min and serially diluted by 2 fold before mixing with 100 $TCID_{50}$ virus (H1N1 NC, or H1N1PR8) in duplicate. After incubation at 37° C. for 1 hr, the mixtures were transferred to MDCK cells in 96 well plates and incubated at 37° C. for 1 hr. The plates were washed once with culture media after removing the mixtures, and fresh media containing 1 μg/ml trypsin was then added. The plates were incubated at 37° C. for 48 hrs and then fixed in formalin and stained by crystal violet. The neutralization titer is the highest dilution with intact cell monolayer.

The results showed that low pH-treated antigens induced lower HAI or NT titers than the untreated control antigen against the homologous virus (H1N1 NC) in correlation with potency loss (Table 6). However, treated antigens were still capable of inducing considerable levels of HAI and NT titers. In particular, the HAI or NT titer by the antigen with 21.1% potency loss (0° C.) was only lower by about 2 fold as compared to that by the untreated antigen. None of the serum samples induced detectable HAI or NT titer against the heterologous H1N1 virus (A/Puerto Rico/8/34, H1N1 PR8) as expected (Table 6).

The mixed antigen which contains the same amount of the untreated and low pH-treated (37° C.) antigens induced similar HAI and NT titers as the untreated antigen (Table 6). This is consistent with that the potency loss of the treated antigen was compensated by addition of the untreated antigen (Table 5).

TABLE 6

Antibody responses as measured by HAI and NT

| | HAI (GMT (StDev)) | | NT (pooled samples) | |
|---|---|---|---|---|
| Groups | A/NC | A/PR8 | A/NC | A/PR8 |
| Control | 238 (178) | <20 | 2560 | <20 |
| 0° C. | 108 (43) | <20 | 1280 | <20 |
| 25° C. | 59 (45) | <20 | 640 | <20 |
| 37° C. | 66 (102) | <20 | 320 | <20 |
| Mix | 215 (103) | <20 | 2560 | <20 |

ELISA

Figure 3:
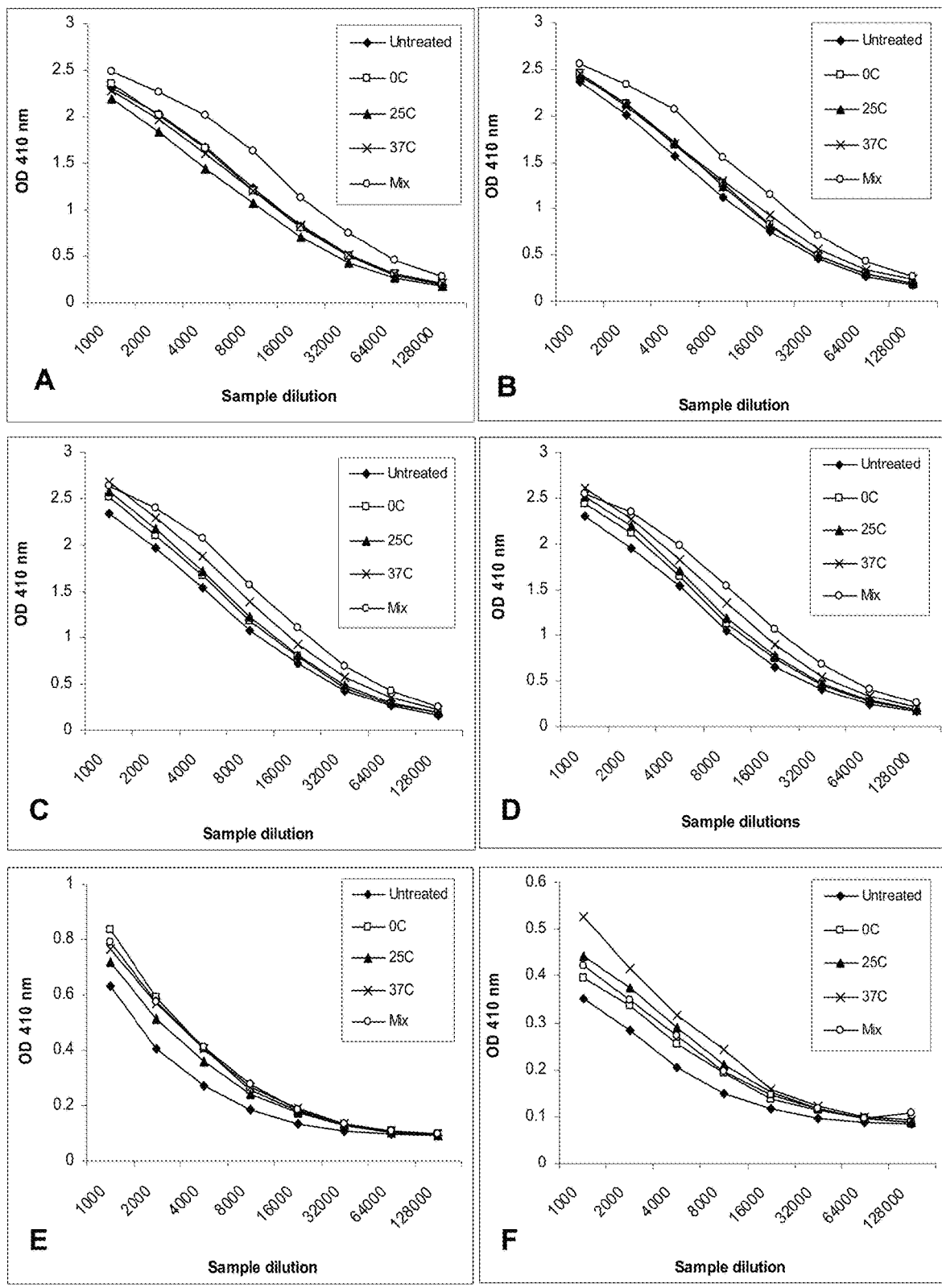
FIG. 3 shows induction of increased cross-reactive antibody responses by low pH-treated antigens. Pooled serum samples generated in mice against inactivated WV antigen (A/New Caledonia/20/99, H1N1 NC) untreated or treated at a low pH (5.1) and different temperatures (0, 25, or 37° C.) or a mixture of antigens consisting of equal amounts of the untreated and the one treated at 37° C. were tested with different antigens in ELISA including the homologous inactivated H1N1 NC WV antigen untreated (A) or treated at pH 5.1 and 0° C. (B), 25° C. (C) or 37° C. (D) and heterologous inactivated H5N3 WV antigen (A/Duck/Singapore-Q/F119-2/97, H5N3 Duck) (E), monovalent 2009 H1N1 pandemic vaccine (A/California/7/2009, H1N1 CA) (F), inactivated H3N2 WV antigen (A/Wisconsin/67/2005) (G), and inactivated B WV antigen (B/Malaysia/2506/2004) (H). The serum samples tested were obtained at week 4 after the $2^{nd}$ immunization.
Figure 3:
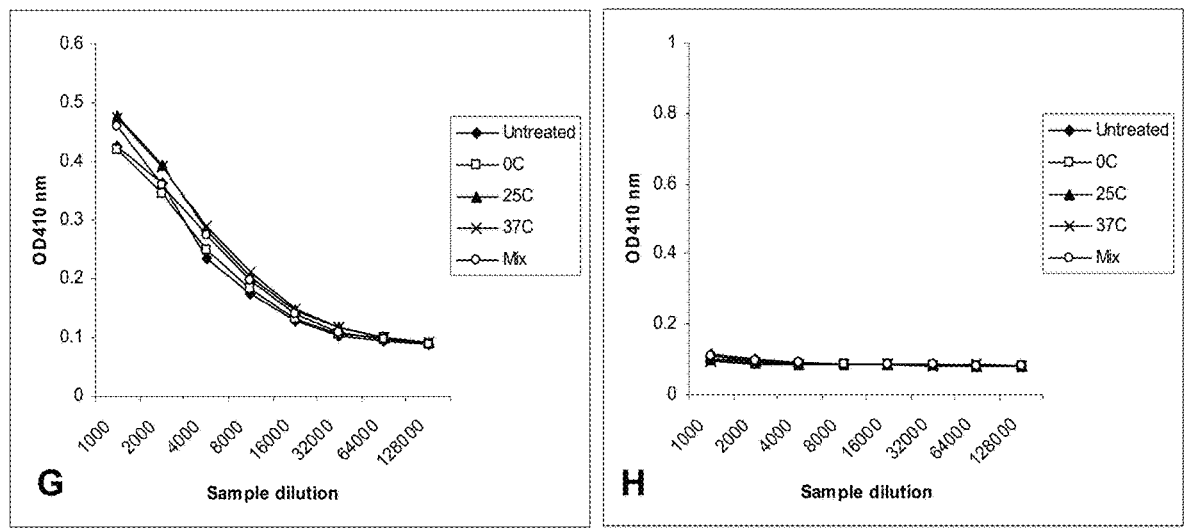

ELISA measures total antigen-binding antibodies. It was performed with untreated or low pH-treated inactivated H1N1 NC WV antigens used to immunize mice as well as heterologous antigens including WV antigens of H5N3 duck (A/Duck/Singapore-Q/F119-2/97), H3N2 Wis, and B Mal, and monovalent 2009 H1N1 pandemic vaccine (A/California/7/2009, H1N1 CA) (Sanofi-Aventis). The 96-well plates were coated (100 μl/well) at 5 μg/ml for WV antigen and 1 μg HA/ml for monovalent vaccine in 0.1 M carbonate buffer (pH 9.6) at 4° C. overnight. Pooled serum samples were serially 2 fold diluted and incubated at room temperature for 2 hrs. After washing, plates were incubated with anti-mouse IgG alkaline phosphatase conjugate for 1 hr, which was followed by washing and incubation with pNPP substrate for 30 min. The OD was measured at 405 nm. All five pooled serum samples were tested at the same time against each of the antigens on the same plate. The titration curves of the serum samples against different antigens are shown in FIG. 3. The data was also analyzed using CDC ELISA program by assigning the serum against untreated antigen 100 arbitrary units and using it as the reference to calculate the units for serum samples against treated antigens for comparison (Table 7 and FIG. 4).

The results showed that the untreated antigen induced antibodies which reacted better with itself than the treated antigens (FIGS. 3A and 4, Table 7), and similarly the treated antigens induced antibodies which reacted better with themselves than the untreated antigen (FIGS. 3B-D and 4, Table 7). This showed that treated antigens were highly immunogenic and at least in part antigenically different from untreated antigen. The highest reaction with treated antigens was induced by the antigen treated at 37° C. and having the largest potency loss (90%) (FIGS. 3B-D and 4, Table 7).

The overall levels of reaction with heterologous antigens were lower as compared to that with the homologous antigen as expected (FIG. 3). However, each of the three treated antigens (pH 5.1 and 0, 25, or 37° C.) induced higher cross reactions with heterologous antigens (H1N1 CA and H5N3 duck) as compared to the untreated antigen (FIGS. 3E-F and 4; Table 7). The antigen treated at 37° C. with a 90% potency loss induced the highest cross reaction, which was >2 fold higher than that by the untreated antigen (FIGS. 3E-F and 4; Table 7). However, a considerable increase in cross reaction (>70%) was also obtained with antigen treated at 0° C. or having only a 21.1% potency loss (FIGS. 3E-F and 4; Table 7). A smaller increase in cross-reaction (<50%) was observed with H3N2 Wis antigen (FIGS. 3G and 4; Table 7). No cross reaction was observed with B Mal antigen (FIG. 3H). The H1 and H5 subtypes belong to phylogenetic group I, whereas the H3 subtype belongs to phylogenetic group II. Thus, the cross reaction induced by low pH-treated antigens appeared to be higher with heterologous antigens from the same phylogenetic group.

Figure 5:
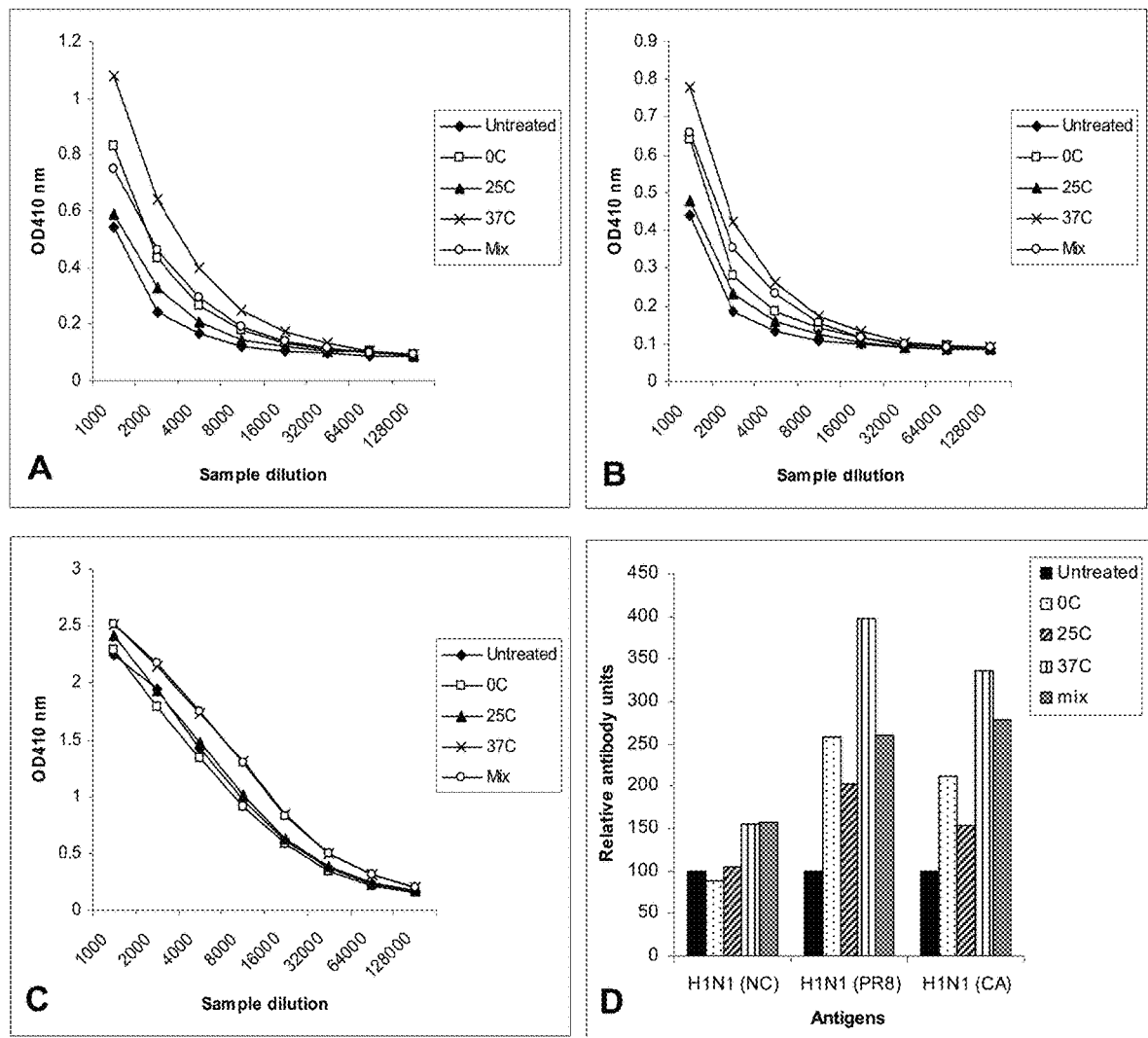
FIG. 5 shows induction of increased cross-reactive antibody responses by low pH-treated antigens. The same pooled serum samples were tested by ELISA as in FIG. 3, but with recombinant HA protein of the heterologous A/Puerto Rico/8/34 (H1N1 PR8) (A) or A/California/7/2009 (H1N1 CA) (B) virus, or the homologous A/New Caledonia/20/99 (H1N1 NC) virus (C). The untreated and treated antigens were compared for induction of cross-reactive antibody responses in the same manner as in FIG. 4 (D).

To further confirm these results, the recombinant HA of homologous H1N1 NC and heterologous H1N1 CA and H1N1 PR8 viruses (Sino-Biologicals) were tested. These recombinant HAs are produced in mammalian cells and consist of the entire ectodomain of the HA. As with inactivated antigens, the overall reaction levels with heterologous recombinant HAs was lower as compared to that with the homologous HA (H1N1 NC) (FIG. 5 and Table 8). However, serum samples against treated antigens exhibited an increased cross reaction with heterologous recombinant HAs (FIG. 5 and Table 8), thus further indicating the ability of treated antigens to induce the increased cross reaction and demonstrating that the increased cross reaction is directed toward the HA. The serum against the antigen treated at 37°

C. exhibited the highest cross reaction with heterologous antigens with a titer nearly 4 fold higher that that with untreated antigen, which was followed by those against antigens treated at 0° C. (2.1-2.6 fold) and 25° C. (1.5-2.0 fold) (FIG. 5 and Table 8).

TABLE 7

Cross-reactive antibody responses by ELISA

| | Serum samples | | | | |
|---|---|---|---|---|---|
| Antigens | Untreated | 0° C. | 25° C. | 37° C. | Mix |
| Untreated | 100 | 99.6 | 75.8 | 97.4 | 178.2 |
| 0° C. | 100 | 117.1 | 115.5 | 134.7 | 198.0 |
| 25° C. | 100 | 118.5 | 125.9 | 158.9 | 208.1 |
| 37° C. | 100 | 118.6 | 129.5 | 160.6 | 208.5 |
| H1N1 CA | 100 | 175.9 | 209.1 | 260.64 | 247.5 |
| H5N3 Duck | 100 | 190.1 | 166.2 | 200.5 | 197.2 |
| H3N2 | 100 | 101.5 | 138.8 | 143.1 | 123.3 |

TABLE 8

Cross-reactive antibody responses by ELISA with recombinant HA antigens

| | Serum samples | | | | |
|---|---|---|---|---|---|
| Antigens | Untreated | 0° C. | 25° C. | 37° C. | Mix |
| H1N1 NC | 100 | 87.9 | 105.1 | 155.5 | 168.8 |
| H1N1 PR8 | 100 | 258.4 | 202.7 | 398.3 | 259.4 |
| H1N1 CA | 100 | 211.4 | 153.3 | 336.5 | 277.6 |

Figure 4:
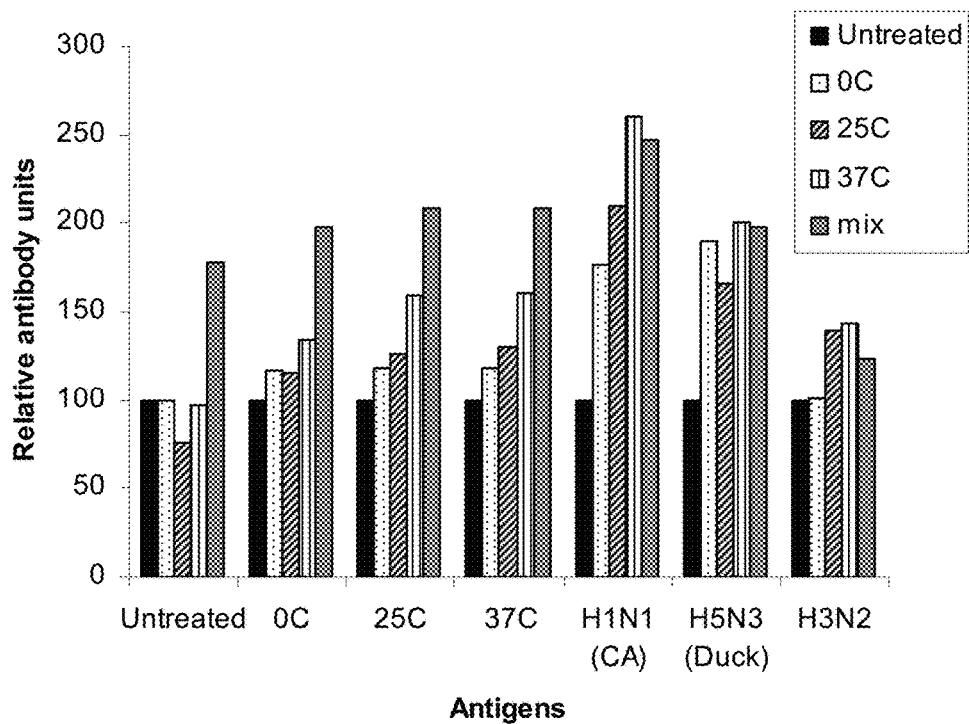
FIG. 4 shows the comparison of untreated and low pH-treated antigens in induction of cross-reactive antibody responses. The ELISA units of the serum samples in FIG. 3 were determined by assigning the serum sample against the untreated antigen arbitrarily 100 units as a reference for calculation of the titers (units) of other serum samples for reacting with the same antigen tested on the same ELISA plate.

The mixed antigens which contain the same amount of the untreated antigen and the one treated at 37° C. consistently induced high levels of responses against both homologous and heterologous antigens tested (FIGS. 3-5 and Tables 7-8), indicating that the mixed antigen can effectively induce responses against both homologous and heterologous antigens.

Immunoblot

Pooled serum samples were also tested by immunoblot against homologous and heterologous antigens. The antigens were separated by SDS-PAGE and then blotted onto a nylon membrane (Immobilon-P, Millipore). The membranes were blocked with blocking buffer containing 3% BSA in PBS with 0.025% Tween 20. The pooled serum sample from each group was diluted in the blocking buffer, and incubated with the membrane for 2 hrs at room temperature. The membrane was then incubated with anti-mouse IgG-alkaline phosphatase conjugate for 1 hr before being washed and reacted with NBT/BCIP substrate. For comparison of relative levels of antibody binding to individual protein bands, the densities of positive bands were measured using the ImageJ program (NIH).

The results showed that treated antigens induced stronger antibody reactions with HA1 and HA2 than the untreated antigen (FIG. 6). Remarkably, antigens treated under different conditions induced distinctly different antibody reaction patterns. The antigen treated at the mild condition (0° C.) with a potency loss of 21.1% induced the largest increase in reaction with HA2, whereas the one treated at 37° C. with a potency loss of 90% induced the largest increase in reaction with HA1 as shown with the homologous H1N1 NC antigen (FIG. 6). An intermediate reaction pattern was obtained with the antigen treated at 25° C. with a potency loss of 66.3%. These distinct reaction patterns were also observed in a separate experiment with similarly treated antigens (see Example 4).

As with ELISA, the overall extent of reaction with heterologous antigens was lower than that with the homologous antigen. However, the highest reaction with HA2 induced by the antigen treated at the mild condition (0° C.) occurred consistently with all heterologous antigens tested, including H1N1 CA and H5N1 VN (A/Vietnam/1203/2004) monovalent vaccines and H5N3 duck WV antigen (FIG. 6), which was as much as >2 fold higher than that by untreated antigen. The increased cross reaction with HA2 was also shown with the baculovirus-expressed recombinant HA (H5N1 VN) which was treated with trypsin to separate HA1 and HA2 prior to use (Wang et al., Vaccine. 24:2176-2185, 2006). On the other hand, the increased reaction with HA1 of different heterologous antigens varied between individual antigens under different treatment conditions (FIG. 6). These results are consistent with the fact that HA2 is much more conserved than HA1. A minor increase in cross reaction with HA2 of the H3N2 Wis was also observed, but no cross reaction was observed with B Mal antigen.

Together, these results showed that the antigen treated at the mild condition (0° C.) induced greater reaction with HA2, whereas the one treated at the more stringent condition (37° C.) induced higher reaction with HA1. This indicates that antigenic or structural changes are not only quantitative, but also qualitative under different low pH treatment conditions. This is also consistent with that the increased cross reaction with HA1 or HA2 as measured by immunoblot does not necessarily correlate with the total cross-reactive antibody levels measured by ELISA.

Example 4

Induction of Increased Cross-Reactive Antibody Responses and Cross Protection by Antigens Treated at Suitable Low pH Conditions A similar experiment as in Example 3 was conducted, but with mice challenged with a heterologous virus at the end of the experiment. The H1N1 NC WV antigens were treated at pH 5.2 and different temperatures (0, 25, or 37° C.). The potency and hemagglutination activity of these antigens are shown in Table 9. The potency reduction of these antigens was similar to that described in Example 3, but was lower for antigens treated at 4 and 25° C. (Table 9). This is consistent with that a slightly higher pH (5.2) was used for the treatment. Groups of 6-8 weeks old female Balb/c mice (n=7) were immunized with treated and untreated antigens as in Example 3. Pooled serum samples were similarly analyzed by ELISA, HAI, NT and immunoblot using the homologous (H1N1 NC) and heterologous (H1N1 PR8) antigens or viruses. The challenge was performed at week 3 after the $2^{nd}$ immunization with H1N1 PR8 virus at a highly lethal dose of $1\times10^6$ $TCID_{50}$ per mouse. After challenge, mice were monitored daily for body weight and survival.

TABLE 9

Potency and hemagglutination titer of inactivated WV antigens (H1N1, NC) obtained after low pH (5.2) treatment.

| Antigens | Total protein (μg/ml) | Potency (HA μg/ml; (% reduction)) | Hemagglutination |
|---|---|---|---|
| Control | 720 | 133.4 (0%) | 5120 |
| 0° C. | 720 | 116.7 (12.5%) | 5120 |
| 25° C. | 720 | 72.74 (45.5%) | 5120 |
| 37° C. | 720 | 13.3 (90.0%) | 5120 |

Cross-Reactive Immune Responses As shown in Example 3, all treated antigens induced increased cross-reactive total antibody responses as measured by ELISA (Table 10). The ELISA titer was determined by the endpoint defined as an OD value at least 2 fold higher than the background. The antigens treated at 25 and 37° C. induced the higher cross reaction with the heterologous H1N1 PR8 antigen as compared to the one treated at 0° C. (Table 10).

TABLE 10

Antibody responses (ELISA, HAI and NT)

| Groups | ELISA | | HAI | | NT | |
|---|---|---|---|---|---|---|
| | H1N1 NC | H1N1 PR8 | H1N1 NC | H1N1 PR8 | H1N1 NC | H1N1 PR8 |
| Control | 128,000 | 8,000 | 320 | <10 | 2560 | <20 |
| 0° C. | 128,000 | 16,000 | 320 | <10 | 2560 | <20 |
| 25° C. | 256,000 | 32,000 | 160 | 10 | 2560 | 20 |
| 37° C. | 256,000 | 32,000 | 160 | <10 | 1280 | <20 |

The antigen treated at 0° C. with a 12.5% potency loss induced the same HAI and NT titers as the untreated antigen, while the one treated at 37° C. induced the lowest HAI and NT titers against the homologous virus (Table 10). The antigen treated at 25° C. exhibited a 2-fold lower HAI titer and the same NT titer (Table 10). This is consistent with the levels of potency reduction obtained. As in example 3, the untreated antigen did not induce any detectable HAI or NT titer against the heterologous H1N1 PR8, further confirming the heterologous nature between these two viruses (232 fold difference by HAI, Table 10). However, the antigen treated at 25° C. did induce a low and yet increased level of HAI and NT titers against the H1N1 PR8.

Figure 7:
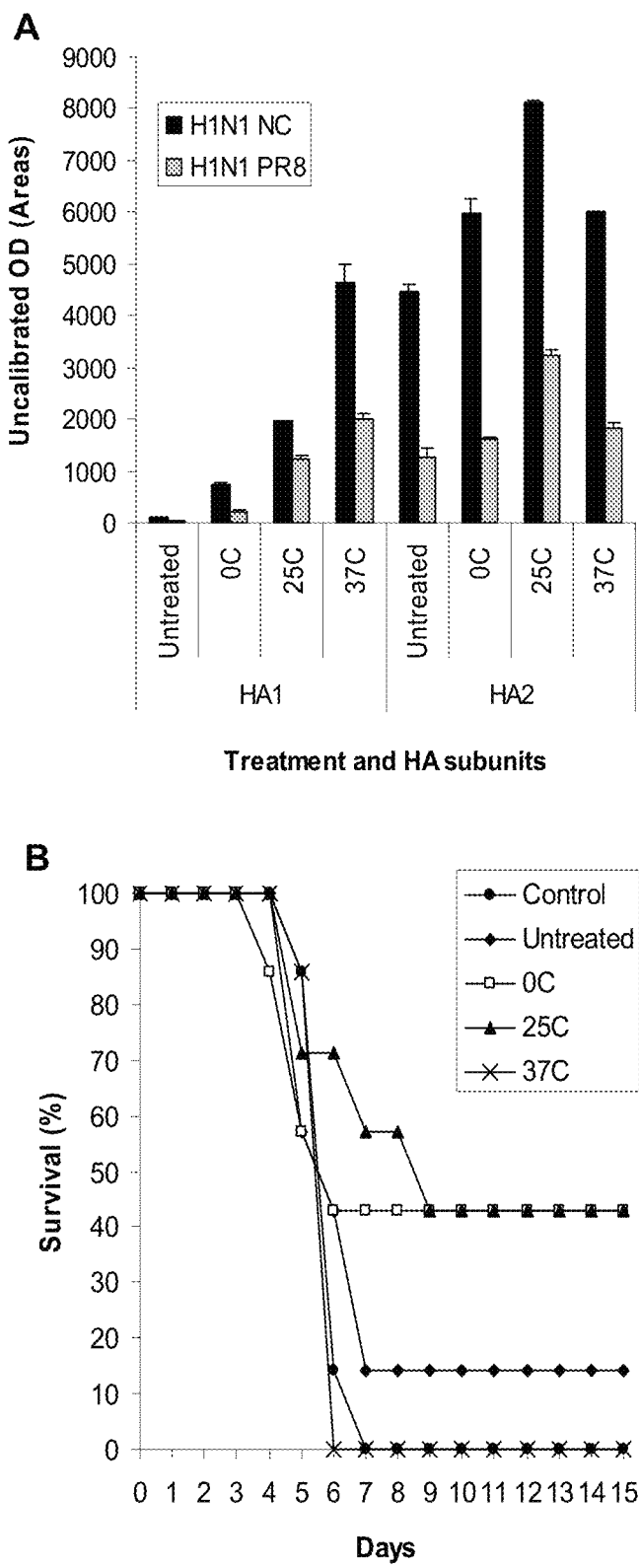
FIG. 7 shows the increased antibody reaction with HA1 and HA2 and cross protection induced by low pH-treated antigens. Panel A shows the plot of densities (uncalibrated OD) of HA1 and HA2 protein bands in the immunoblot. The pooled serum sample against the untreated or low pH-treated (pH5.2 at 0, 25, or 37° C.) inactivated WV antigen (A/New Caledonia/20/99, H1N1 NC) was tested with the homologous (H1N1 NC) and heterologous (H1N1 PR8) antigens by immunoblot. The serum samples tested were obtained at week 2 after the $2^{nd}$ immunization. Panel B shows the cross-protection against the lethal challenge with the heterologous H1N1 PR8 virus. The challenge was performed at week 3 after the 2n immunization.

The immunoblot results showed that as in the Example 3, all treated antigens induced increased reactions with HA1 and HA2. The antigen treated at 37° C. with a potency loss of 90% induced the highest reaction or cross reaction with HA1 of the homologous H1N1 NC or heterologous H1N1 PR8, whereas the highest level of such reaction or cross reaction with HA2 was obtained with the antigen treated at 25° C. or having a potency loss of 45.5% (FIG. 7A). Together with results in Example 3 showing that the highest cross reaction with HA2 was induced by the antigen treated at pH5.1 and 0° C. with a potency loss of 21.1%, these results indicate that treated antigens with a potency loss of 20-50% are particularly effective in inducing higher cross reaction with HA2.

Cross Protection

The challenge results showed that antigens treated at 0 and 25° C. provided a much increased cross protection (43% or 3/7) as compared to the untreated antigen (14% or 1/7) (FIG. 7B). In contrast and unexpectedly, no detectable cross protection was obtained with the antigen treated at 37° C. (FIG. 7B). The antigen treated at 25° C. provided the overall best cross protection as mice with this antigen survived longer (FIG. 7B) and those recovered gained weight earlier and faster, reaching >90% of the original body weight by the end of the two-week observation. As shown above, the antigens treated at 0 and 25° C. exhibited a potency loss of 12.5 and 45.5%, respectively, and induced the increased cross reaction with HA2 with the highest level by the antigen treated at 25° C. Thus, the increased cross protection is associated with the partial potency loss (<50%) and the increased cross reaction with HA2.

Although partial, the level of the increased cross protection by antigens treated at mild conditions (0 and 25° C.) was obtained under the strong challenge condition and without use of any adjuvant (FIG. 7B). Such increased cross protection could be highly significant in the event of a pandemic or emergence of a highly infectious seasonal variant virus. It is highly unexpected that the antigen treated at 37° C. did provide any detectable cross protection. It may have a weaker cross protection which however could not be detected under the strong challenge condition used (FIG. 7B). It is possible that antigens treated at mild conditions may have only gained limited antigenic or structural changes which are suited for better exposure of HA2 and possibly other conserved domains in their native forms and consequently increase cross reaction and protection, whereas those treated at 37° C. may have gained excessive antigenic or structural changes as evidenced by the nearly complete potency loss and therefore may be less relevant to the native HA and consequently less protective.

Example 5

Protease Sensitivity of the Low pH-Treated Antigens

It is known that low pH treatment induces the structural changes of HA which render it sensitive to protease digestion (Carr et al., Proc. Natl. Acad. Sci. USA 94:14306-14313, 1997).

Figure 8:
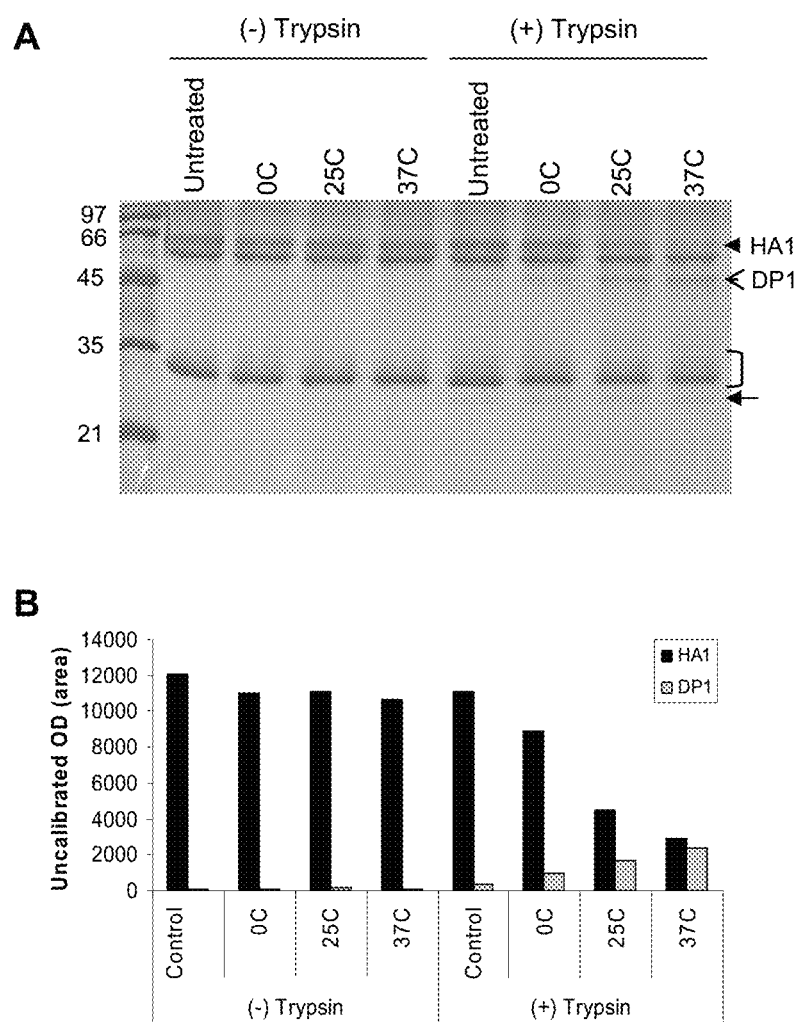
FIG. 8 shows the protease sensitivity of untreated and low pH-treated (pH5.2 at 0, 25, or 37° C.) inactivated WV antigens (A/New Caledonia/20/99, H1N1 NC). Panel A shows the gel stained with Commassie blue; panel B shows the plot of densities of protein bands. The closed arrow head indicates the HA1, open arrow head indicates the HA1 digestion product (DP1), the bracket indicates the HA2/M1, and closed arrow indicates the trypsin.

Thus, the untreated and low-pH treated antigens prepared in Example 4 were mixed with trypsin (10 μg/ml) and incubated at room temperature for 30 min. The antigens were then separated by SDS-PAGE and stained with Coommassie blue. The results showed that HA in untreated antigen was resistant to trypsin digestion, whereas the HA1 in treated antigens was gradually digested in correlation with treatment conditions (FIG. 8). The HA1 in the antigen treated at 37° C. disappeared almost completely, whereas majority of HA1 in the antigen treated at 0° C. remained intact. About 50% of HA1 in the antigen treated at 25° C. was digested. The gradual disappearance of HA1 is correlated with the gradual appearance of its degradation product (DP1, FIG. 8). The change in HA2 could not be clearly detected as it co-migrated with the M1 protein (FIG. 8). These results therefore showed that like potency loss, the protease sensitivity increased in direct correlation with the low pH treatment conditions.

Example 6

Formulation of Low pH-Treated Antigens as a Vaccine

An influenza antigen comprising HA is first treated under a suitable low pH or other suitable conditions to obtain an appropriate level of potency loss or antigenic or structural changes. It is then formulated with pharmaceutically acceptable excipients or carriers as a vaccine for induction of the increased cross-reactive immune response and cross protection. The vaccine may be monovalent or multivalent by incorporating treated antigens from one or more strains. A suitable adjuvant may be incorporated to further enhance the cross-reactive immune responses and cross protection. The suitable adjuvant may be selected from polysaccharides such as lipopolysaccharide and saponin, nucleic acids such as CpG and poly I:C, lipids such as MPL (monophosphoryl Lipid A), proteins such as bacterial flagellin, inorganic salts such as aluminum salts and calcium phosphate, emulsions such as incomplete Freund, MF59 and AS03, and various Toll-like receptor ligands. Different adjuvants may be tested with the treated antigen to identify the suitable ones at appropriate adjuvant doses which generate higher levels of cross-reactive immune responses and cross protection, including the complete or 100% protection. At the same time, the use of a suitable adjuvant will also increase the strain-specific immune responses, allowing the vaccine to induce the same or even higher level of such responses as with the untreated antigens or like current inactivated vaccines (see below).

The vaccine may also be formulated to meet the potency standard so that the resulting vaccine will not only provide an increased cross-reactive immune response and cross protection, but also the same level of strain-specific protection like the current inactivated vaccines. This dual-effect vaccine can be produced by compensating the partial potency loss of treated antigens through different approaches. One approach is to mix treated antigen with a suitable amount of untreated antigen to meet the potency standard. As shown in Example 3 with the antigen treated at 37° C. and having a potency loss of 290%, a mixture of the treated and untreated antigens can be prepared with expected levels of potency and immunogenicity. As an example, for a treated antigen with a 20% potency loss, 20% more of the untreated antigen with intact potency may be added for the vaccine to meet the potency standard.

Another approach is to use a proportionally increased amount of the treated antigens based on the extent of potency loss. For example, for a treated antigen with a 20% potency loss, only 25% more of this same antigen is needed to meet the potency standard. The antigens treated at the mild conditions (0-25° C.) and having a potency loss less than 50% may be preferred to conserve the antigen use. This approach has one distinct advantage in that only one antigen component is used. In addition, with the presence of more treated antigens, the vaccine may induce a higher level of cross-reactive immune responses and cross protection.

One additional approach is to formulate the treated antigen with a suitable adjuvant which may include those described above. Adjuvants increase immune responses and thereby reduce the amount of antigen or the level of potency required to achieve the same level of immune responses and protection. For inactivated influenza vaccines, the amount of antigen required to achieve protection in humans can be reduced by several folds from the standard 15 μg HA to as low as 1.5 μg HA through use of a suitable adjuvant (Cox et al., Vaccine. 29:8049-8059, 2011; Garcon et al., Expert Rev Vaccines. 11:349-366, 2012). Thus, incorporation of a suitable adjuvant can allow the treated antigen to further increase the cross-reactive immune responses and cross protection, and at the same time also induce the same level of strain-specific immune responses and protection like the untreated antigen without the need for any additional antigens.

Example 7

Low pH Treatment of Recombinant HA

Recombinant HA of H3N2 Wis (A/Wisconsin/67/2005) produced in baculovirus (BEI Resources) were treated at pH 5.2 and different temperatures (0, 25, or 37° C.) as described in Examples 1 and 2. The potency of treated antigens was determined by SRD as described in Example 1. As with inactivated WV antigen and TIV, low pH treatment decreased the potency of the recombinant HA in correlation with treatment conditions. Thus, the potency was lost completely (100%) at 37° C., by 93.1% at 25° C., and 36.6% at 0° C. (Table 11). These results indicated that the potency of recombinant HA can also be gradually reduced in correlation with the low pH treatment conditions.

TABLE 11

Potency of recombinant HA (H3N2 Wis) treated at pH 5.2 and different temperatures as indicated by precipitation ring sizes.

| | Temperatures | | | |
|---|---|---|---|---|
| | Control | 0° C. | 25° C. | 37° C. |
| Precipitation ring size (mm²)* (% reduction) | 25.9 (0%) | 16.4 (36.6%) | 1.8 (93.1%) | 0 (100%) |

*Excluding the area of the center well.

Example 8

Treatment of Influenza Antigens at High Temperatures

The inactivated WV antigen of H1N1 NC in PBS (pH7.2) was placed in 250 μl tubes (100 μl/tube) and heated in a PCR (polymerase chain reaction) machine for 10 min at different temperatures. The potency and hemagglutination activity of untreated and treated antigens were evaluated as described in Example 1.

The results showed that the potency decreased along with increase in temperature (Table 12). The potency decreased by 14.8% at 50° C. and 75.7% at 68° C. Relatively low levels of potency loss (<21%) were obtained when the antigen was treated at 62° C. or lower. Once the temperature reached 264° C., the potency reduction dramatically accelerated along with increase in temperature by every two degrees (Table 12). The hemagglutination titer started to decrease at 66° C. (63.4% potency reduction) and was lower by 4 fold at 68° C. (75.7% potency reduction). Compared to the low pH treatment (Examples 1 and 2), the hemagglutination titer appeared to decrease much faster with the high temperature treatment in relation to the degree of potency loss, suggesting that antigen denaturing might occur at higher temperatures.

TABLE 12

Treatment of inactivated WV antigens (H1N1, NC) at different temperatures.

| | Temperatures (° C.) | | | | | | |
|---|---|---|---|---|---|---|---|
| | Control | 50 | 60 | 62 | 64 | 66 | 68 |
| Precipitation ring size (mm²)* (% reduction) | 20.4 (0%) | 17.4 (14.8%) | 17.1 (16%) | 16.2 (20.7%) | 12.3 (39.8%) | 7.5 (63.4%) | 5.0 (75.7%) |
| Hemagglutination titer | 1280 | 1280 | 1280 | 1280 | 1280 | 640 | 320 |

*Excluding the area of the center well.

The invention claimed is:

1. A method of producing an inactivated influenza vaccine with an ability to induce increased cross-reactive immune response and cross protection, the method comprising the steps of: (a) providing at least one influenza hemagglutinin-containing antigen and a pharmaceutically acceptable carrier; (b) subjecting said antigen to treatment at a pH at or below 6.8 and a temperature below 37° C. to obtain a loss of potency of less than 100%; and (c) inactivating said antigen with a chemical agent either before or after said treatment thereby producing a vaccine that increases cross-reactive immune response and cross protection; (d) testing the vaccine for the ability to induce an increased cross-reactive immune response and cross protection; and e) determining that said vaccine has the ability to induce an increased cross-reactive immune response and cross-protection.

2. The method of claim 1, wherein said vaccine comprises at least two said antigens selected from a group comprising H1 and H3 subtypes of influenza A virus.

3. The method of claim 1, wherein said vaccine comprises at least three said antigens selected from a group comprising at least two clades from phylogenetic group I and at least one clade from phylogenetic group II, wherein each said antigen is selected from a separate clade.

4. The method of claim 1, wherein said antigen is a live virus, and said live virus is inactivated after said treatment.

5. The method of claim 1, wherein said pH ranges from 3.0 to 6.8.

6. The method of claim 1, wherein said treatment is conducted at a temperature of 2-8° C.

7. The method of claim 1, wherein said treatment is conducted at a temperature of 0-25° C.

8. The method of claim 1, wherein said antigen exhibits no or less than 2-fold reduction in hemagglutination activity after said treatment.

9. The method of claim 1, wherein said loss of potency ranges from 1 to less than 100%.

10. The method of claim 1, wherein said loss of potency ranges from 10 to 50%.

11. The method of claim 10, wherein said treatment is conducted at a temperature of 0-25° C.

12. The method of claim 1, wherein said loss of potency is correlated with antigenic or structural changes of said antigen.

13. The method of claim 1, wherein said vaccine induces an increased immune response against HA2 as compared to untreated antigen.

14. The method of claim 1, wherein said vaccine is formulated for induction of a strain-specific immune response and protection.

15. The method of claim 1, wherein said vaccine further comprises an adjuvant.

16. The method of claim 1, wherein the chemical agent is selected from a group comprising formaldehyde, glutaraldehyde, beta-propiolactone, and Triton X-100.

17. A method of producing a recombinant influenza vaccine for induction of an increased cross-reactive immune response and cross-protection against influenza virus comprising providing at least one influenza hemagglutinin-containing antigen and a pharmaceutically acceptable carrier, wherein said antigen is subjected to treatment at a pH at or below 6.8 and a temperature below 37° C. to obtain a loss of potency of less than 100%, thereby producing the vaccine, testing the vaccine for the ability to induce an increased cross-reactive immune response and cross protection and determining that said vaccine has the ability to induce an increased cross-reactive immune response and cross-protection.

18. The method of claim 17, wherein said vaccine induces an increased immune response against HA2 as compared to untreated antigen.

19. The method of claim 17, wherein said vaccine is formulated for induction of a strain-specific immune response and protection.

20. The method of claim 17, wherein said vaccine further comprises an adjuvant.

21. The method of claim 17, wherein the recombinant influenza vaccine is not inactivated.

22. A method of vaccinating a subject, the method comprising providing the vaccine produced by the method comprising the steps of (a) providing at least one influenza hemagglutinin-containing antigen and a pharmaceutically acceptable carrier; (b) subjecting said antigen to treatment at a pH at or below 6.8 and a temperature below 37° C. to obtain a loss of potency of less than 100%; (c) inactivating said antigen with a chemical agent either before or after said treatment, thereby producing a vaccine with increased cross-reactive immune response and cross protection; and administering the said vaccine to the subject.

23. A method of vaccinating a subject, the method comprising providing the vaccine produced by the method of claim 17 to the subject.

24. The method of claim 22, wherein the vaccine is tested for its ability to induce an increased cross-reactive immune response and cross-protection against influenza virus; and determined to have that ability, before it is administered to the subject.

* * * * *